(12) United States Patent
Tomono et al.

(10) Patent No.: US 7,351,556 B2
(45) Date of Patent: Apr. 1, 2008

(54) α-AGARASE AND PROCESS FOR PRODUCING THE SAME

(75) Inventors: Jun Tomono, Muko (JP); Yoshiko Nomura, Kyoto (JP); Hiroaki Sagawa, Kusatsu (JP); Takeshi Sakai, Hirosaki (JP); Ikunoshin Kato, Uji (JP)

(73) Assignee: Takara Bio Inc., Shiga (JP)

( * ) Notice: Subject to any disclaimer, the term of this patent is extended or adjusted under 35 U.S.C. 154(b) by 0 days.

(21) Appl. No.: 11/553,912

(22) Filed: Oct. 27, 2006

(65) Prior Publication Data
US 2007/0166804 A1    Jul. 19, 2007

Related U.S. Application Data

(60) Division of application No. 10/464,488, filed on Jun. 19, 2003, now Pat. No. 7,141,402, which is a division of application No. 09/924,097, filed on Aug. 8, 2001, now Pat. No. 6,599,729, which is a continuation-in-part of application No. PCT/JP00/00966, filed on Feb. 21, 2000.

(30) Foreign Application Priority Data

Feb. 23, 1999 (JP) .................................. 11-044890
Jul. 13, 1999 (JP) .................................. 11-198852

(51) Int. Cl.
C12P 19/44   (2006.01)
C12N 9/24    (2006.01)

(52) U.S. Cl. ........................................ 435/74; 435/200
(58) Field of Classification Search ............... None
See application file for complete search history.

(56) References Cited

U.S. PATENT DOCUMENTS 5,834,257 A    11/1998   Sugano et al.

FOREIGN PATENT DOCUMENTS

| JP | 02-234671 A | 9/1990 |
| JP | 7 322878 | 12/1995 |
| JP | 7 322886 | 12/1995 |
| JP | 2001-275685 A | 10/2001 |

OTHER PUBLICATIONS

Flament et al. (Jan. 21, 2000) GenBank accession AF 121273.*
Potin et al., "Purification and Characterization of the α-agarase from *Alteromonas agarlyticus* (Cataldi) comb. nov., strain GJ1B", *Eur. J. Biochem.*, (1993), vol. 214, pp. 599-607.
Kwan S. Young et al "Enzymic Cleavage of the α-Linkages in Agrose, to Yield Agaro-Oligosaccharides" Carbohydrate Reseach, vol. 66, pp. 207-212, 1978.

* cited by examiner

*Primary Examiner*—Elizabeth Slobodyansky
(74) *Attorney, Agent, or Firm*—Browdy and Neimark, PLLC

(57) ABSTRACT

A polypeptide having an α-agarase activity, a gene encoding the polypeptide, a method for producing the polypeptide by genetic engineering and a method for producing an agarooligosaccharide using the polypeptide.

2 Claims, 2 Drawing Sheets

1 2 3 4 5

```
                          SEQUENCE LISTING

<160> NUMBER OF SEQ ID NOS: 30

<210> SEQ ID NO 1
<211> LENGTH: 10
<212> TYPE: PRT
<213> ORGANISM: Unknown
<220> FEATURE:
<223> OTHER INFORMATION: N-terminal amino acid sequence of agarase 4-3

<400> SEQUENCE: 1

Asp Thr Leu Ser Val Glu Ala Glu Met Phe
1               5                   10

<210> SEQ ID NO 2
<211> LENGTH: 20
<212> TYPE: PRT
<213> ORGANISM: Unknown
<220> FEATURE:
<223> OTHER INFORMATION: Designed oligonucleotide primer for PCR using
      pAA1 as template

<400> SEQUENCE: 2

Gly Asp Ile Val Ile Glu Leu Glu Asp Phe Asp Ala Thr Gly Thr Thr
1               5                   10                  15

Gly Arg Val Ala
            20
```

```
<210> SEQ ID NO 3
<211> LENGTH: 30
<212> TYPE: DNA
<213> ORGANISM: Unknown
<220> FEATURE:
<223> OTHER INFORMATION: Designed oligonucleotide primer for PCR using
      pAA1 as template
<220> FEATURE:
<221> NAME/KEY: misc_feature
<222> LOCATION: (6)..(6)
<223> OTHER INFORMATION: Unknown
<220> FEATURE:
<221> NAME/KEY: misc_feature
<222> LOCATION: (9)..(9)
<223> OTHER INFORMATION: Unknown
<220> FEATURE:
<221> NAME/KEY: misc_feature
<222> LOCATION: (12)..(12)
<223> OTHER INFORMATION: Unknown
<220> FEATURE:
<221> NAME/KEY: misc_feature
<222> LOCATION: (15)..(15)
<223> OTHER INFORMATION: Unknown
<220> FEATURE:
<221> NAME/KEY: misc_feature
<222> LOCATION: (21)..(21)
<223> OTHER INFORMATION: Unknown

<400> SEQUENCE: 3
gayacnytnt cngtngargc ngaratgtty                                30

<210> SEQ ID NO 4
<211> LENGTH: 17
<212> TYPE: DNA
<213> ORGANISM: Unknown
<220> FEATURE:
<223> OTHER INFORMATION: Designed oligonucleotide primer for PCR using
      pAA1 as template

<400> SEQUENCE: 4
gttttcccag tcacgac                                              17

<210> SEQ ID NO 5
<211> LENGTH: 30
<212> TYPE: DNA
<213> ORGANISM: Unknown
<220> FEATURE:
<223> OTHER INFORMATION: Designed oligonucleotide primer for DNA
      sequencing of pAA1

<400> SEQUENCE: 5
attgatgtcg taatcaacat agtccccgc                                 30

<210> SEQ ID NO 6
<211> LENGTH: 30
<212> TYPE: DNA
<213> ORGANISM: Unknown
<220> FEATURE:
<223> OTHER INFORMATION: Designed oligonucleotide primer for amplifying
      DNA fragment 4-3N
<220> FEATURE:
<221> NAME/KEY: misc_feature
<222> LOCATION: (9)..(9)
<223> OTHER INFORMATION: Unknown
<220> FEATURE:
<221> NAME/KEY: misc_feature
<222> LOCATION: (18)..(18)
<223> OTHER INFORMATION: Unknown

<400> SEQUENCE: 6
gayathgtna thgarctnga rgayttygay                                30
```

```
<210> SEQ ID NO 7
<211> LENGTH: 26
<212> TYPE: DNA
<213> ORGANISM: Unknown
<220> FEATURE:
<223> OTHER INFORMATION: Designed oligonucleotide primer for amplyifying
      DNA fragment 4-3N
<220> FEATURE:
<221> NAME/KEY: misc_feature
<222> LOCATION: (3)..(3)
<223> OTHER INFORMATION: Unknown
<220> FEATURE:
<221> NAME/KEY: misc_feature
<222> LOCATION: (6)..(6)
<223> OTHER INFORMATION: Unknown
<220> FEATURE:
<221> NAME/KEY: misc_feature
<222> LOCATION: (9)..(9)
<223> OTHER INFORMATION: Unknown
<220> FEATURE:
<221> NAME/KEY: misc_feature
<222> LOCATION: (12)..(12)
<223> OTHER INFORMATION: Unknown
<220> FEATURE:
<221> NAME/KEY: misc_feature
<222> LOCATION: (15)..(15)
<223> OTHER INFORMATION: Unknown
<220> FEATURE:
<221> NAME/KEY: misc_feature
<222> LOCATION: (18)..(18)
<223> OTHER INFORMATION: Unknown
<220> FEATURE:
<221> NAME/KEY: misc_feature
<222> LOCATION: (21)..(21)
<223> OTHER INFORMATION: Unknown
<220> FEATURE:
<221> NAME/KEY: misc_feature
<222> LOCATION: (24)..(24)
<223> OTHER INFORMATION: Unknown

<400> SEQUENCE: 7
gcnacnggna cnacnggnmg ngtngc                                          26

<210> SEQ ID NO 8
<211> LENGTH: 30
<212> TYPE: DNA
<213> ORGANISM: Unknown
<220> FEATURE:
<223> OTHER INFORMATION: Designed oligonucleotide primer for cloning DNA
      fragment 4-3UN

<400> SEQUENCE: 8
gttacccagc tgacattggt tgcacccgcc                                      30

<210> SEQ ID NO 9
<211> LENGTH: 30
<212> TYPE: DNA
<213> ORGANISM: Unknown
<220> FEATURE:
<223> OTHER INFORMATION: Designed oligonucleotide primer for cloning DNA
      fragment 4-3UN

<400> SEQUENCE: 9
gctgcaacga aaccatcatt aggatcactg                                      30

<210> SEQ ID NO 10
<211> LENGTH: 30
<212> TYPE: DNA
<213> ORGANISM: Unknown
<220> FEATURE:
<223> OTHER INFORMATION: Designed oligonucleotide primer for cloning DNA
      fragment 4-3C
```

<400> SEQUENCE: 10
gagtgttacc aacaacagca atggtgatgc                                      30

<210> SEQ ID NO 11
<211> LENGTH: 30
<212> TYPE: DNA
<213> ORGANISM: Unknown
<220> FEATURE:
<223> OTHER INFORMATION: Designed oligonucleotide primer for cloning DNA
      fragment 4-3C

<400> SEQUENCE: 11
gtaatcacgg ttaacaactt agaggtgtgg                                      30

<210> SEQ ID NO 12
<211> LENGTH: 2778
<212> TYPE: DNA
<213> ORGANISM: Unknown
<220> FEATURE:
<223> OTHER INFORMATION: Nucleotide sequence of ORF in agarase 1-7 gene

<400> SEQUENCE: 12
atgaataaaa atatcaagct atcactgctt agtatggggg ttttatgctc tgctggtcta      60
gtgactaaca ttgctgttgc agataccta tctgttgaag cagaaatgtt tagcaattca     120
gggggaacat ttgctgatgg ccaagctaat ccaattacca tttacacagt taatggtgag     180
caggcgatta gttatgtcaa tgcgggggac tatgttgatt acgacatcaa taccgaaggg     240
ggcgactact cagttgaata tcttgtcggg acaagtgttg cttctggccc gacaatagaa     300
atgctagtaa agaaaatgg tgtttgggta agtcaaggta cagtcgctgt tccacaaggc     360
agttgggata actttcaacc actttcaccg tcacatttag taaccttacc tgcaggtgcc     420
gcttcaattc gccttcatgc cataggttca aattggcaat ggaacttaga gtcttttcc     480 ttaacacaag taacaccact acctggcgct tccgtagctg atgtagtggt agagttagaa     540
aactttatta atactgataa agaccgcaat gctattgctg gtgattctgt ggtgggtttt     600
ggcaccacta acaatggcat taactttaat acccttggtg attacgctga ctatcatgtc     660
aattttgcta gcccaggtac ctataatgta tccattgctg ctggttcaac ggttcaaggg     720
caaataggcg cagaaatttt actgaatggt ataccgttg cttcaaatta tctgtcagca     780
acagcaggtt gggatgatta ccaagatttt gcgctgactg gtgatgtaat aattgctaat     840
gctgggactc ataccataag agtaaaaagc tacggtagtg caaattggca atggaatggt     900
gactctatta ccttcactca tatttcggat gacaccaacg gcggcagcaa ccaagcaatg     960
catctagaac caccttatgc gataccagag agccgtaaaa ttaaaaaatc ttctgtatgg    1020
tacacctacc cacaaaaactc taatttagct ggctttagtg actttggtgc taccggcgct    1080
ttctggggac acatgccaga agaagatcta acgatagtg gcgtgctttc taactggttt    1140
aaccaagtac aagggtatcg caatcaaggt ttagactatg ttggtcgtgg tgaatttgat    1200 tggggttca gatggtttat tgaatatgtt ggcgacccta catcacactg gcacgaacg    1260 ttagacgatg atcccatttt aatgtctttt atgggatacc atgaacacaa tggttatctg    1320
aacggctggt taagtaacca tagccccacc tttgttgatt ttttttaagtc tcaagttgat    1380 gccttattaa gcgctaacgt ttcacacatc atgtttgatt cgcaaacttc atcgacgcga    1440
tctaccgatt taggccaatt tggtggcgat ttctctactt ggtcaatgga tgcttttcgt    1500
gaatatatgc gtgataaata caccacagcc gagttaaaca ccaaaggcat aactaatatc    1560

```
aatgcgttta attatcgaaa cttttttaaga agtcgaggct acacccatgc ttcgtatatg    1620
gctgctgcca ataaaatcac tagtggcata ccattgtttg atgattttat ttattttaat    1680
cgtgctgtgc taaatgaaaa aatggcagaa gtactggatt atatccgctc aattgatgct    1740
gatattgaaa ttggcgcgac caccgcttta accgaagcac gtggctatat ttttgataaa    1800
gacctaactt tcttagccgg tgaattagcc atgggttcag cggttgctga cgaaatgcca    1860
ataccaatta tttcacactt aaaaagtgct gaagccgttg ataaaacgct cgtttacttc    1920
ccttatcctt ggaactttaa agacctgtac gaccgtaatt cgcctcaaat ggcacgaact    1980
tggattgctc aatcgtatgc tatgggggca atattctcaa tccctgccaa cgtttggata    2040
ggtgatgctg gcgtttggtc acctggtgct gataattatc gcgatctcta tcaatttgcc    2100
agcgacaata gcgcattact tgatggttat gatgcctttt ctaaggttgg gttagtttca    2160
cctatgatgg cttcacttga taccacatgg attgatggta gcaatcgttt acaaacgagt    2220
atccgttacc ttattgaaaa taacttaaac tttgatttat taatttttgg tgaccctggt    2280
aaacccgtag tccctactca agcacaatta tctgcactag atgcgattat tgttgatagt    2340
gatcgcaagt acttaaccga cgcacaaaat gccttgttag atgcaaataa tcagaaagta    2400
ttggacttaa acaacagtgc tgataccgcc gccattaatg ccctgaaagc aacaaatata    2460
tcagtgacta tcggtaatgc cgctgctgat gatacgatta ctgcgctttc tcgtgtgcat    2520
gaaagcaata ataacgcgcc ttatgttatt cagttattaa atcgtcctgt taatccagcc    2580
aatggtgtaa caccagtatt aagtaatgtt aaaattgcta ttccacaagg ctattttcct    2640
gaaggaataa cacaagcaac cgtgcataaa cctggcgccg gctcggtcaa tgccaatatt    2700
acctcaaata caatggtgga ttatgttatt accgttaata atttaggggt ttggggaatg    2760
attgaattag cgcattaa                                                   2778
```

```
<210> SEQ ID NO 13
<211> LENGTH: 2856
<212> TYPE: DNA
<213> ORGANISM: Unknown
<220> FEATURE:
<223> OTHER INFORMATION: Nucleotide sequence of ORF in agarase 4-3 gene

<400> SEQUENCE: 13
```

```
atgaaatcca acaaaaaacg cagagtactc ggagttgcta tccctctcac atacacatta     60
ttacttagtt ttagcaattc agccttgagc gaaacactaa ttgttcaagc cgaatccttt    120
acccattcag gaggcacctt taacgatggg caatcctccc ccatcagtat ttatactgtt    180
aacggtgaac aagcaattag ctgggtcaac gctggtgatt atgttgacta taacgtcacc    240
gcagttggcg gtgaatataa catcgagtat ttggttggaa catctgtagc ggctaacccg    300
attatcgaag tattggttga cagtaatggt acttttgaga gccaaggtac ggttattgtg    360
ccattaggta gttgggacga tttccaacca cttgtagctg cgcacacggt gacactgcca    420
gcgggcacct caactatacg cttgcatgct attggtccag attggcaatg gaatttagag    480
tcattttcac tgactggtgg ctcagaaaca ggtagtggcg atatagttga ttcggtcctt    540
ccgcctctgg gtgatattgt cattgagcta aagactttg atgccacagg tacaaccggc    600
agagtggcca gtgatcctaa tgatggtttc gttgcagcgg cgggtgcaac caatgtcagc    660
tgggtaacca acggtgattt cggcgactac aataacatct accttgaagc tgggacttat    720
cgttcgttta ttacggtagc aactggcagc gacggtagct atggtgcacg cattgaccta    780
```

```
gatggttcgc cggcttcctg gggttacttt gatagtactg gtggctggga aaccccagag     840
gaagtcgagc tttatggcgg tgattttgta gttgaaacaa gtggcactca tacattacgt     900
gtagaagcca ttggtggctc agattggcaa tggagcggtg ataacgttcg cctcactaaa     960
gtgggcgacg catctgtcaa accatcacct ttgtataatc ctaaagacca taccgttaca    1020
gaaattgaag gtcctgtcgt tggtttacca tttttgaaaa aaccagttca ggttccaaca    1080
gccaacagat tgttgaaatc agacgtatgg tatacctatc ctcaaaataa cgagctgcaa    1140
ggttttgata atttcggtgc aacaggttca ttttggggcc atcctccaga gaaaatttc    1200
tacgatgaca ccaccataat tgattggaca caactcgttc aaaactatca aggaataggc    1260
attgaataca ctgctcgcgg cgaatttgat tggggcttcc gctgggttac tgaatacttg    1320
actaatcccg aaccccatta tgtaaaaaca cttgatgatc gcaatgtgcg aatgacgttc    1380
atgggttacc tcagttataa cggctacaac aacaactggt tgagtaatca cagtccagcg    1440
tttgtgccgc acatgaagtc acaagtggat caaatactaa gagccaaccc agacaagctg    1500
atgtttgata cacaaaccaa ctctactcgt tcaaccgaca tgcgcacttt cggggggtgat    1560
ttcaacgatt atgccatggc aaacttccgt gtttggctag ataaaaaata tagtagctca    1620
gaactttcag ctatgggtat tgataatatt gcaaccttta actatcgtga tttcttgtta    1680
gctagagggg taacgcacac atcatttctt aatgctgcag ataccatttc aggtgacgtt    1740
cctttgcttg aggatttcat ctacttcaat cgagatgttt ggaatcaaaa gtttgctgaa    1800
gtgttagatt acattcgcat gcaacgtcca aacatcgaga taggtgcaag cacacatttg    1860
tttgaatctc gtggttacat atttaacgag aacatcaccct tcttatcggg tgaattaaat    1920
ttgggtgcca gaaccaccat agctgaacta cccaccaata ttcttgttca cttaaaaggc    1980
gcgcaagctg tcgataaacc cttggcgtat ttcccatacc cttgggagtt cgccgaatta    2040
cgtgaccaaa atgcgccgcg ttttggtcgt ggttgggttg ctcaggctta tgcctacgga    2100
gggttgttct caatccctgc taacgtatgg gttggcggca atacaggtga aaacacgtgg    2160
tcacctggcg ccgataacta tcgcgacatt taccaatttg ttcgtgcgca atcaaatttg    2220
tttgacaact acacttcata cgcaaaagta gggcttgttc atgccatgta ttcatcaatg    2280
aaggcaggtt ttatcgatgg tgtaatcaa attcagtcaa gcgtgaaact tctaactgaa    2340
gacaacatca actttgactt attagtgttt ggcgatgagg gttatccggt tgtgcctcgc    2400
actgaagact tcaatcagtt tgcgcatata ttctatgacg gcgaccttag ttacttaact    2460
gcagagcagc aagctgtgct agatcaacag ggctctaaag taaaacacat aggtcaacgc    2520
ggaacattaa ctggtatcga catcaatgtg agtattaatg gttcactttc taatgaaact    2580
gtatcagcgg tatcccgcat tcatgaaaca aataccaatg cacctatgt tgtacatttα    2640
ataaaccgac cttttctcggg tggcgtcacg ccaatactta gcggagttga agttgctatt    2700
cctcaaggat acttccctga agatgtaacg tctgcaacct tgcattacc tgatggtaca    2760
agcaccaacc tgagtgttac caacaacagc aatggtgatg cagtaatcac ggttaacaac    2820
ttagaggtgt ggggaattct tgaattagct cactaa                              2856
```

<210> SEQ ID NO 14
<211> LENGTH: 925
<212> TYPE: PRT
<213> ORGANISM: Unknown
<220> FEATURE:
<223> OTHER INFORMATION: Amino acid sequence of agarase 1-7

<400> SEQUENCE: 14

-continued

```
Met Asn Lys Asn Ile Lys Leu Ser Leu Leu Ser Met Gly Val Leu Cys
1               5                   10                  15

Ser Ala Gly Leu Val Thr Asn Ile Ala Val Ala Asp Thr Leu Ser Val
            20                  25                  30

Glu Ala Glu Met Phe Ser Asn Ser Gly Gly Thr Phe Ala Asp Gly Gln
        35                  40                  45

Ala Asn Pro Ile Thr Ile Tyr Thr Val Asn Gly Glu Gln Ala Ile Ser
    50                  55                  60

Tyr Val Asn Ala Gly Asp Tyr Val Asp Tyr Asp Ile Asn Thr Glu Gly
65                  70                  75                  80

Gly Asp Tyr Ser Val Glu Tyr Leu Val Gly Thr Ser Val Ala Ser Gly
                85                  90                  95

Pro Thr Ile Glu Met Leu Val Lys Glu Asn Gly Val Trp Val Ser Gln
            100                 105                 110

Gly Thr Val Ala Val Pro Gln Gly Ser Trp Asp Asn Phe Gln Pro Leu
        115                 120                 125

Ser Pro Ser His Leu Val Thr Leu Pro Ala Gly Ala Ala Ser Ile Arg
    130                 135                 140

Leu His Ala Ile Gly Ser Asn Trp Gln Trp Asn Leu Glu Ser Phe Ser
145                 150                 155                 160

Leu Thr Gln Val Thr Pro Leu Pro Gly Ala Ser Val Ala Asp Val Val
                165                 170                 175

Val Glu Leu Glu Asn Phe Ile Asn Thr Asp Lys Asp Arg Asn Ala Ile
            180                 185                 190

Ala Gly Asp Ser Val Val Gly Phe Gly Thr Thr Asn Asn Gly Ile Asn
        195                 200                 205

Phe Asn Thr Leu Gly Asp Tyr Ala Asp Tyr His Val Asn Phe Ala Ser
    210                 215                 220

Pro Gly Thr Tyr Asn Val Ser Ile Ala Ala Gly Ser Thr Val Gln Gly
225                 230                 235                 240

Gln Ile Gly Ala Glu Ile Leu Leu Asn Gly Asn Thr Val Ala Ser Asn
                245                 250                 255

Tyr Leu Ser Ala Thr Ala Gly Trp Asp Asp Tyr Gln Asp Phe Ala Leu
            260                 265                 270

Thr Gly Asp Val Ile Ile Ala Asn Ala Gly Thr His Thr Ile Arg Val
        275                 280                 285

Lys Ser Tyr Gly Ser Ala Asn Trp Gln Trp Asn Gly Asp Ser Ile Thr
    290                 295                 300

Phe Thr His Ile Ser Asp Asp Thr Asn Gly Gly Ser Asn Gln Ala Met
305                 310                 315                 320

His Leu Glu Pro Pro Tyr Ala Ile Pro Glu Ser Arg Lys Ile Lys Lys
                325                 330                 335

Ser Ser Val Trp Tyr Thr Tyr Pro Gln Asn Ser Asn Leu Ala Gly Phe
            340                 345                 350

Ser Asp Phe Gly Ala Thr Gly Ala Phe Trp Gly His Met Pro Glu Glu
        355                 360                 365

Asp Leu Tyr Asp Ser Gly Val Leu Ser Asn Trp Val Asn Gln Val Gln
    370                 375                 380

Gly Tyr Arg Asn Gln Gly Leu Asp Tyr Val Gly Arg Gly Glu Phe Asp
385                 390                 395                 400

Trp Gly Phe Arg Trp Phe Ile Glu Tyr Val Gly Asp Pro Thr Ser His
                405                 410                 415
```

-continued

```
Trp Ala Arg Thr Leu Asp Asp Pro Ile Leu Met Ser Phe Met Gly
            420                 425                 430

Tyr His Glu His Asn Gly Tyr Leu Asn Gly Trp Leu Ser Asn His Ser
        435                 440                 445

Pro Thr Phe Val Asp Phe Phe Lys Ser Gln Val Asp Ala Leu Leu Ser
    450                 455                 460

Ala Asn Val Ser His Ile Met Phe Asp Ser Gln Thr Ser Ser Thr Arg
465                 470                 475                 480

Ser Thr Asp Leu Gly Gln Phe Gly Gly Asp Phe Ser Thr Trp Ser Met
            485                 490                 495

Asp Ala Phe Arg Glu Tyr Met Arg Asp Lys Tyr Thr Thr Ala Glu Leu
        500                 505                 510

Asn Thr Lys Gly Ile Thr Asn Ile Asn Ala Phe Asn Tyr Arg Asn Phe
    515                 520                 525

Leu Arg Ser Arg Gly Tyr Thr His Ala Ser Tyr Met Ala Ala Ala Asn
    530                 535                 540

Lys Ile Thr Ser Gly Ile Pro Leu Phe Asp Asp Phe Ile Tyr Phe Asn
545                 550                 555                 560

Arg Ala Val Leu Asn Glu Lys Met Ala Glu Val Leu Asp Tyr Ile Arg
            565                 570                 575

Ser Ile Asp Ala Asp Ile Glu Ile Gly Ala Thr Thr Ala Leu Thr Glu
        580                 585                 590

Ala Arg Gly Tyr Ile Phe Asp Lys Asp Leu Thr Phe Leu Ala Gly Glu
    595                 600                 605

Leu Ala Met Gly Ser Ala Val Ala Asp Glu Met Pro Ile Pro Ile Ile
    610                 615                 620

Ser His Leu Lys Ser Ala Glu Ala Val Asp Lys Thr Leu Val Tyr Phe
625                 630                 635                 640

Pro Tyr Pro Trp Asn Phe Lys Asp Leu Tyr Asp Arg Asn Ser Pro Gln
            645                 650                 655

Met Ala Arg Thr Trp Ile Ala Gln Ser Tyr Ala Met Gly Ala Ile Phe
        660                 665                 670

Ser Ile Pro Ala Asn Val Trp Ile Gly Asp Ala Gly Val Trp Ser Pro
    675                 680                 685

Gly Ala Asp Asn Tyr Arg Asp Leu Tyr Gln Phe Ala Ser Asp Asn Ser
    690                 695                 700

Ala Leu Leu Asp Gly Tyr Asp Ala Phe Ser Lys Val Gly Leu Val Ser
705                 710                 715                 720

Pro Met Met Ala Ser Leu Asp Thr Thr Trp Ile Asp Gly Ser Asn Arg
            725                 730                 735

Leu Gln Thr Ser Ile Arg Tyr Leu Ile Glu Asn Asn Leu Asn Phe Asp
        740                 745                 750

Leu Leu Ile Phe Gly Asp Pro Gly Lys Pro Val Val Pro Thr Gln Ala
    755                 760                 765

Gln Leu Ser Ala Leu Asp Ala Ile Ile Val Asp Ser Asp Arg Lys Tyr
    770                 775                 780

Leu Thr Asp Ala Gln Asn Ala Leu Leu Asp Ala Asn Asn Gln Lys Val
785                 790                 795                 800

Leu Asp Leu Asn Asn Ser Ala Asp Thr Ala Ile Asn Ala Leu Lys
            805                 810                 815

Ala Thr Asn Ile Ser Val Thr Ile Gly Asn Ala Ala Ala Asp Asp Thr
        820                 825                 830

Ile Thr Ala Leu Ser Arg Val His Glu Ser Asn Asn Asn Ala Pro Tyr
```

```
                 835                 840                 845
Val Ile Gln Leu Leu Asn Arg Pro Val Asn Pro Ala Asn Gly Val Thr
             850                 855                 860

Pro Val Leu Ser Asn Val Lys Ile Ala Ile Pro Gln Gly Tyr Phe Pro
865                 870                 875                 880

Glu Gly Ile Thr Gln Ala Thr Val His Lys Pro Gly Ala Gly Ser Val
                885                 890                 895

Asn Ala Asn Ile Thr Ser Asn Asn Gly Asp Tyr Val Ile Thr Val
            900                 905                 910

Asn Asn Leu Gly Val Trp Gly Met Ile Glu Leu Ala His
            915                 920                 925

<210> SEQ ID NO 15
<211> LENGTH: 951
<212> TYPE: PRT
<213> ORGANISM: Unknown
<220> FEATURE:
<223> OTHER INFORMATION: Amino acid sequence of agarase 4-3

<400> SEQUENCE: 15

Met Lys Ser Asn Lys Lys Arg Arg Val Leu Gly Val Ala Ile Pro Leu
1               5                   10                  15

Thr Tyr Thr Leu Leu Leu Ser Phe Ser Asn Ser Ala Leu Ser Glu Thr
            20                  25                  30

Leu Ile Val Gln Ala Glu Ser Phe Thr His Ser Gly Gly Thr Phe Asn
        35                  40                  45

Asp Gly Gln Ser Ser Pro Ile Ser Ile Tyr Thr Val Asn Gly Glu Gln
50                  55                  60

Ala Ile Ser Trp Val Asn Ala Gly Asp Tyr Val Asp Tyr Asn Val Thr
65                  70                  75                  80

Ala Val Gly Gly Glu Tyr Asn Ile Glu Tyr Leu Val Gly Thr Ser Val
                85                  90                  95

Ala Ala Asn Pro Ile Ile Glu Val Leu Val Asp Ser Asn Gly Thr Phe
            100                 105                 110

Glu Ser Gln Gly Thr Val Ile Val Pro Leu Gly Ser Trp Asp Asp Phe
        115                 120                 125

Gln Pro Leu Val Ala Ala His Thr Val Thr Leu Pro Ala Gly Thr Ser
130                 135                 140

Thr Ile Arg Leu His Ala Ile Gly Pro Asp Trp Gln Trp Asn Leu Glu
145                 150                 155                 160

Ser Phe Ser Leu Thr Gly Gly Ser Glu Thr Gly Ser Gly Asp Ile Val
                165                 170                 175

Asp Ser Val Leu Pro Pro Leu Gly Asp Ile Val Ile Glu Leu Glu Asp
            180                 185                 190

Phe Asp Ala Thr Gly Thr Thr Gly Arg Val Ala Ser Asp Pro Asn Asp
        195                 200                 205

Gly Phe Val Ala Ala Gly Ala Thr Asn Val Ser Trp Val Thr Asn
210                 215                 220

Gly Asp Phe Gly Asp Tyr Asn Asn Ile Tyr Leu Glu Ala Gly Thr Tyr
225                 230                 235                 240

Arg Ser Phe Ile Thr Val Ala Thr Gly Ser Asp Gly Ser Tyr Gly Ala
                245                 250                 255

Arg Ile Asp Leu Asp Gly Ser Pro Ala Ser Trp Gly Tyr Phe Asp Ser
            260                 265                 270

Thr Gly Gly Trp Glu Thr Pro Glu Glu Val Glu Leu Tyr Gly Gly Asp
```

-continued

```
                275                 280                 285
Phe Val Val Glu Thr Ser Gly Thr His Thr Leu Arg Val Glu Ala Ile
290                     295                 300
Gly Gly Ser Asp Trp Gln Trp Ser Gly Asp Asn Val Arg Leu Thr Lys
305                 310                 315                 320
Val Gly Asp Ala Ser Val Lys Pro Ser Pro Leu Tyr Asn Pro Lys Asp
                325                 330                 335
His Thr Val Thr Glu Ile Glu Gly Pro Val Val Gly Leu Pro Phe Leu
                340                 345                 350
Lys Lys Pro Val Gln Val Pro Thr Ala Asn Arg Leu Leu Lys Ser Asp
355                 360                 365
Val Trp Tyr Thr Tyr Pro Gln Asn Asn Glu Leu Gln Gly Phe Asp Asn
370                 375                 380
Phe Gly Ala Thr Gly Ser Phe Trp Gly His Pro Glu Glu Asn Phe
385                 390                 395                 400
Tyr Asp Asp Thr Thr Ile Ile Asp Trp Thr Gln Leu Val Gln Asn Tyr
                405                 410                 415
Gln Gly Ile Gly Ile Glu Tyr Thr Ala Arg Gly Glu Phe Asp Trp Gly
                420                 425                 430
Phe Arg Trp Val Thr Glu Tyr Leu Thr Asn Pro Glu Pro His Tyr Val
                435                 440                 445
Lys Thr Leu Asp Asp Arg Asn Val Arg Met Thr Phe Met Gly Tyr Leu
                450                 455                 460
Ser Tyr Asn Gly Tyr Asn Asn Trp Leu Ser Asn His Ser Pro Ala
465                 470                 475                 480
Phe Val Pro His Met Lys Ser Gln Val Asp Gln Ile Leu Arg Ala Asn
                485                 490                 495
Pro Asp Lys Leu Met Phe Asp Thr Gln Thr Asn Ser Thr Arg Ser Thr
                500                 505                 510
Asp Met Arg Thr Phe Gly Gly Asp Phe Asn Asp Tyr Ala Met Ala Asn
                515                 520                 525
Phe Arg Val Trp Leu Asp Lys Lys Tyr Ser Ser Ser Glu Leu Ser Ala
                530                 535                 540
Met Gly Ile Asp Asn Ile Ala Thr Phe Asn Tyr Arg Asp Phe Leu Leu
545                 550                 555                 560
Ala Arg Gly Val Thr His Thr Ser Phe Ser Asn Ala Ala Asp Thr Ile
                565                 570                 575
Ser Gly Asp Val Pro Leu Leu Glu Asp Phe Ile Tyr Phe Asn Arg Asp
                580                 585                 590
Val Trp Asn Gln Lys Phe Ala Glu Val Leu Asp Tyr Ile Arg Met Gln
                595                 600                 605
Arg Pro Asn Ile Glu Ile Gly Ala Ser Thr His Leu Phe Glu Ser Arg
610                 615                 620
Gly Tyr Ile Phe Asn Glu Asn Ile Thr Phe Leu Ser Gly Glu Leu Asn
625                 630                 635                 640
Leu Gly Ala Arg Thr Thr Ile Ala Glu Leu Pro Thr Asn Ile Leu Val
                645                 650                 655
His Leu Lys Gly Ala Gln Ala Val Asp Lys Pro Leu Ala Tyr Phe Pro
                660                 665                 670
Tyr Pro Trp Glu Phe Ala Glu Leu Arg Asp Gln Asn Ala Pro Arg Phe
                675                 680                 685
Gly Arg Gly Trp Val Ala Gln Ala Tyr Ala Tyr Gly Gly Leu Phe Ser
690                 695                 700
```

```
Ile Pro Ala Asn Val Trp Val Gly Gly Asn Thr Gly Glu Asn Thr Trp
705                 710                 715                 720

Ser Pro Gly Ala Asp Asn Tyr Arg Asp Ile Tyr Gln Phe Val Arg Ala
            725                 730                 735

Gln Ser Asn Leu Phe Asp Asn Tyr Thr Ser Tyr Ala Lys Val Gly Leu
        740                 745                 750

Val His Ala Met Tyr Ser Ser Met Lys Ala Gly Phe Ile Asp Gly Gly
    755                 760                 765

Asn Gln Ile Gln Ser Ser Val Lys Leu Leu Thr Glu Asp Asn Ile Asn
770                 775                 780

Phe Asp Leu Leu Val Phe Gly Asp Glu Gly Tyr Pro Val Pro Arg
785                 790                 795                 800

Thr Glu Asp Phe Asn Gln Phe Ala His Ile Phe Tyr Asp Gly Asp Leu
            805                 810                 815

Ser Tyr Leu Thr Ala Glu Gln Gln Ala Val Leu Asp Gln Gln Gly Ser
        820                 825                 830

Lys Val Lys His Ile Gly Gln Arg Gly Thr Leu Thr Gly Ile Asp Ile
    835                 840                 845

Asn Val Ser Ile Asn Gly Ser Leu Ser Asn Glu Thr Val Ser Ala Val
850                 855                 860

Ser Arg Ile His Glu Thr Asn Thr Asn Ala Pro Tyr Val Val His Leu
865                 870                 875                 880

Ile Asn Arg Pro Phe Ser Gly Gly Val Thr Pro Ile Leu Ser Gly Val
            885                 890                 895

Glu Val Ala Ile Pro Gln Gly Tyr Phe Pro Glu Asp Val Thr Ser Ala
        900                 905                 910

Thr Leu His Leu Pro Asp Gly Thr Ser Thr Asn Leu Ser Val Thr Asn
    915                 920                 925

Asn Ser Asn Gly Asp Ala Val Ile Thr Val Asn Asn Leu Glu Val Trp
930                 935                 940

Gly Ile Leu Glu Leu Ala His
945                 950

<210> SEQ ID NO 16
<211> LENGTH: 20
<212> TYPE: DNA
<213> ORGANISM: Unknown
<220> FEATURE:
<223> OTHER INFORMATION: Designed oligonucleotide primer for amplifying
      DNA fragment from 16S ribosomal

<400> SEQUENCE: 16
agagtttgat cctggctcag                                              20

<210> SEQ ID NO 17
<211> LENGTH: 19
<212> TYPE: DNA
<213> ORGANISM: Unknown
<220> FEATURE:
<223> OTHER INFORMATION: Designed oligonucleotide primer for amplifying
      DNA fragment from 16S ribosomal

<400> SEQUENCE: 17
ggctaccttg ttacgactt                                               19

<210> SEQ ID NO 18
<211> LENGTH: 26
<212> TYPE: DNA
```

<213> ORGANISM: Unknown
<220> FEATURE:
<223> OTHER INFORMATION: Designed oligonucleotide for constructing
     plasmid for expressing agarase 1-7

<400> SEQUENCE: 18
gctgttgcat atggataccc tatctg                                              26

<210> SEQ ID NO 19
<211> LENGTH: 32
<212> TYPE: DNA
<213> ORGANISM: Unknown
<220> FEATURE:
<223> OTHER INFORMATION: Designed oligonucleotide for constructing
     plasmid for expressing agarase 1-7

<400> SEQUENCE: 19
gctgttgcca tggataccct atctgttgaa gc                                       32

<210> SEQ ID NO 20
<211> LENGTH: 36
<212> TYPE: DNA
<213> ORGANISM: Unknown
<220> FEATURE:
<223> OTHER INFORMATION: Designed oligonucleotide for constructing
     plasmid for expressing agarase 1-7

<400> SEQUENCE: 20
cggatcgggg atcctgcgct aattcaatca ttcccc                                   36

<210> SEQ ID NO 21
<211> LENGTH: 29
<212> TYPE: DNA
<213> ORGANISM: Unknown
<220> FEATURE:
<223> OTHER INFORMATION: Designed oligonucleotide for constructing
     plasmid for expressing agarase 4-3

<400> SEQUENCE: 21
cggtccttcc gcatatgggt gatattgtc                                           29

<210> SEQ ID NO 22
<211> LENGTH: 30
<212> TYPE: DNA
<213> ORGANISM: Unknown
<220> FEATURE:
<223> OTHER INFORMATION: Synthetic

<400> SEQUENCE: 22
gctgtatgga tcctatctgc aaacggtgcg                                          30

<210> SEQ ID NO 23
<211> LENGTH: 35
<212> TYPE: DNA
<213> ORGANISM: Unknown
<220> FEATURE:
<223> OTHER INFORMATION: Designed oligonucleotide for construcing
     plasmid for expressing agarase 4-3

<400> SEQUENCE: 23
gtactcaagg gatcctgagc taattcaaga attcc                                    35

<210> SEQ ID NO 24
<211> LENGTH: 32
<212> TYPE: DNA
<213> ORGANISM: Unknown
<220> FEATURE:

<223> OTHER INFORMATION: Desinged oligonucleotide for constructing
    plasmid for expressing agarase 1-7

<400> SEQUENCE: 24
ccgtagctga tcatatggta gagttagaaa ac                            32

<210> SEQ ID NO 25
<211> LENGTH: 36
<212> TYPE: DNA
<213> ORGANISM: Unknown
<220> FEATURE:
<223> OTHER INFORMATION: Designed oligonucleotide for construcing
    plasmid for expressing agarase 1-7

<400> SEQUENCE: 25
gtggtgggtt tcatatggg caccactaac aatggc                         36

<210> SEQ ID NO 26
<211> LENGTH: 35
<212> TYPE: DNA
<213> ORGANISM: Unknown
<220> FEATURE:
<223> OTHER INFORMATION: Designed oligonucleotide for constructing
    plasmid for expressing agarase 1-7

<400> SEQUENCE: 26
gccgtaaaat tcatatgaaa aaatcttctg tatgg                         35

<210> SEQ ID NO 27
<211> LENGTH: 37
<212> TYPE: DNA
<213> ORGANISM: Unknown
<220> FEATURE:
<223> OTHER INFORMATION: Designed oligonucleotide for constructing
    plasmid for expressing agarase 1-7

<400> SEQUENCE: 27
gctttctaac catatgtggg ttaaccaagt acaaggg                       37

<210> SEQ ID NO 28
<211> LENGTH: 35
<212> TYPE: DNA
<213> ORGANISM: Unknown
<220> FEATURE:
<223> OTHER INFORMATION: Designed oligonucleotide for constructing
    plasmid for expressing agarase 4-3

<400> SEQUENCE: 28
gcaactggca gccatatgga cggtagctat ggtgc                         35

<210> SEQ ID NO 29
<211> LENGTH: 38
<212> TYPE: DNA
<213> ORGANISM: Unknown
<220> FEATURE:
<223> OTHER INFORMATION: Designed oligonucleotide for constructing
    plasmid for expressing agarase 4-3

<400> SEQUENCE: 29
cagccaacag attgcatatg ttgaaatcag acgtatgg                      38

<210> SEQ ID NO 30
<211> LENGTH: 33
<212> TYPE: DNA
<213> ORGANISM: Unknown
<220> FEATURE:

```
<223> OTHER INFORMATION: Designed oligonucleotide for constructing
      plasmid for expressing agarase 4-3

<400> SEQUENCE: 30
ccataattga tcatatgtgg acacaactcg ttc                                33
```

α-AGARASE AND PROCESS FOR PRODUCING THE SAME

CROSS-REFERENCE TO RELATED APPLICATIONS

This application is a divisional of application Ser. No. 10/464,488, filed Jun. 19, 2003, now U.S. Pat. No. 7,141,402 which is a divisional of parent application Ser. No. 09/924,097, filed Aug. 8, 2001, now U.S. Pat. No. 6,599,729 which is a continuation-in-part application of PCT international application No. PCT/JP00/00966 which has an international filing date of Feb. 21, 2000 which designated the United States, the entire contents of which are incorporated by reference.

BACKGROUND OF THE INVENTION

1. Field of the Invention

The present invention relates to an α-agarase and a method for producing the same. Specifically, the present invention relates to an α-agarase, which is useful for producing agarooligosaccharides with low degrees of polymerization having various physiological activities from agarose, and a method for producing the α-agarase as well as use of the enzyme. The present invention also relates to a polypeptide having an α-agarase activity and a gene encoding said polypeptide. Specifically, the present invention relates to an amino acid sequence of an α-agarase, which is useful for producing agarooligosaccharides with low degrees of polymerization having various physiological activities from agarose, and a nucleotide sequence encoding the amino acid sequence. Furthermore, the present invention relates to a method for producing a polypeptide having an α-agarase activity by genetic engineering. In addition, the present invention relates to a method for producing an agarooligosaccharide using a polypeptide having an α-agarase activity.

2. Description of Related Art

Agarose is the principal constituent of agar. Agarose is a polysaccharide that has a structure in which D-galactose and 3,6-anhydro-L-galactose are alternately linked together through α-1,3 bonds and β-1,4 bonds. One must degrade agarose into smaller molecules in order to produce oligosaccharides from agar. For this purpose, methods in which agarose is chemically degraded and methods in which agarose is enzymatically digested are known. In a chemical degradation method, agarose can be hydrolyzed using an acid. In this case, α-1,3 bonds are mainly cleaved. Two enzymes, β-agarase which cleaves β-1,4 bonds in agarose and α-agarase which cleaves α-1,3 bonds in agarose, are known to digest agarose.

Oligosaccharides obtained by cleaving agarose at β-1,4 bonds are called as neoagarooligosaccharides. Neoagarooligosaccharides have D-galactose at their reducing ends and their degrees of polymerization are expressed by even numbers. On the other hand, oligosaccharides obtained by cleaving agarose at α-1,3 bonds are called as agarooligosaccharides. Agarooligosaccharides have 3,6-anhydro-L-galactose at their reducing ends and their degrees of polymerization are expressed by even numbers. Recently, it was shown that agarooligosaccharides which have 3,6-anhydro-L-galactose at their reducing ends have physiological activities such as an apoptosis-inducing activity, a carcinostatic activity, various antioxidant activities, an immunoregulatory activity, an antiallergic activity, an anti-inflammatory activity and an activity of inhibiting α-glycosidase (WO99/24447, Japanese Patent Application No. 11-11646). Based on the physiological activities, pharmaceutical compositions and functional foods or drinks containing the agarooligosaccharides as their active ingredients can be provided.

It is difficult to control the size of produced oligosaccharides in a method in which agarose is chemically degraded. In particular, it is quite difficult to selectively produce smaller oligosaccharides with low degrees of polymerization (e.g., T. Tokunaga et al., Bioscience & Industry, 49:734 (1991)). If β-agarase is used, only neoagarooligosaccharides which do not have the above-mentioned physiological activities can be obtained because this enzyme cleaves only β-1,4 bonds.

It is expected that agarooligosaccharides having physiological activities are produced by using α-agarase which has an activity of cleaving α-1,3 bonds. Known α-agarases include enzymes produced by a marine Gram-negative bacterial strain GJ1B (Carbohydrate Research, 66:207-212 (1978); this strain is indicated as Alteromonas agarlyticus strain GJ1B in European Journal of Biochemistry, 214:599-607 (1993)) and a bacterium of genus Vibrio (JP-A 7-322878; strain JT0107-L4). However, it is impossible to produce agarobiose which has notable physiological activities by using the α-agarase derived from Alteromonas agarlyticus strain GJ1B because the enzyme cannot digest hexasaccharides or shorter oligosaccharides. Furthermore, the α-agarase derived from a bacterium of genus Vibrio cannot be used for the production of agarooligosaccharides using agarose as a raw material because this enzyme exhibits its activity only on hexasaccharides and shorter oligosaccharides and does not act on agarose at all.

As described above, prior art has problems regarding the production of smaller agarooligosaccharides such as agarobiose and agarotetraose which have 3,6-anhydro-L-galactose at their reducing ends and have various physiological activities.

The main object of the present invention is to provide a polypeptide having an α-agarase activity which can be used for efficient production of smaller agarooligosaccharides, an amino acid sequence of the polypeptide, a gene encoding the polypeptide, a method for producing the polypeptide and a method for producing the smaller agarooligosaccharides.

SUMMARY OF THE INVENTION

In view of the problems as described above, the present inventors have studied intensively and conducted search in order to obtain an enzyme that cleaves α-1,3 bonds in agarose and generates agarooligosaccharides having notable physiological activities. As a result, the present inventors have successfully found two microbial strains that produce enzymes having properties suitable for this purpose. The enzymes produced by these microorganisms were isolated and their physical and chemical as well as enzymatic properties were elucidated. Furthermore, the present inventors have successfully isolated genes for the enzymes, and found a method for readily producing polypeptides having α-agarase activities by means of genetic engineering using the genes, thereby completing the present invention.

The present invention is outlined as follows. The first aspect of the present invention relates to a novel α-agarase having the following physical and chemical properties:

(1) action: hydrolyzing an α-1,3 bond between 3,6-anhydro-L-galactose and D-galactose;

(2) substrate specificity: acting on agarose, agarohexaose and agarooligosaccharides longer than agarohexaose but not on agarotetraose;

(3) optimal temperature: exhibiting its enzymatic activity at a temperature of 55° C. or below; and (4) heat stability: retaining 20% or more of its activity after treatment at 48° C. for 30 seconds.

Such α-agarases are exemplified by an enzyme that contains an amino acid sequence consisting of 749 residues from amino acid number 177 to amino acid number 925 in the amino acid sequence of SEQ ID NO:14, or an amino acid sequence in which one or more amino acids are substituted, deleted, added and/or inserted in said amino acid sequence consisting of 749 residues, or an enzyme that contains an amino acid sequence consisting of 767 residues from amino acid number 184 to amino acid number 950 in the amino acid sequence of SEQ ID NO:15, or an amino acid sequence in which one or more amino acids are substituted, deleted, added and/or inserted in said amino acid sequence consisting of 767 residues.

The second aspect of the present invention relates to a gene encoding a polypeptide having an α-agarase activity, which encodes the α-agarase of the first aspect. Such genes are exemplified by a gene that contains a nucleotide sequence consisting of 2247 bases from base number 529 to base number 2775 in the nucleotide sequence of SEQ ID NO:12, or a nucleotide sequence in which one or more bases are substituted, deleted, added and/or inserted in said nucleotide sequence consisting of 2247 bases, or a gene that contains a nucleotide sequence consisting of 2301 bases from base number 550 to base number 2850 in the nucleotide sequence of SEQ ID NO:13, or a nucleotide sequence in which one or more bases are substituted, deleted, added and/or inserted in said nucleotide sequence consisting of 2301 bases.

The third aspect of the present invention relates to a gene that is hybridizable to the gene of the second aspect under stringent conditions and encodes the α-agarase of the first aspect.

The fourth aspect of the present invention relates to a recombinant DNA molecule that contains the gene of the second or third aspect.

The fifth aspect of the present invention relates to a transformant harboring the recombinant DNA molecule of the fourth aspect.

The sixth aspect of the present invention relates to a method for producing a polypeptide having an α-agarase activity, comprising culturing a microorganism capable of producing an α-agarase (e.g., a microorganism belonging to a genus to which a microorganism TKR1-7AGα (FERM BP-6990) or a microorganism TKR4-3AGα (FERM BP-6991) belongs) and collecting the α-agarase of the first aspect from the culture. Both of the microorganisms TKR1-7AGα and TKR4-3AGα were deposited under Budapest Treaty on Jan. 26, 1999 (the date of the original deposit) at the National Institute of Bioscience and Human-Technology, Agency of Industrial Science and Technology, Ministry of International Trade and Industry, 1-3, Higashi 1-chome, Tsukuba-shi, Ibaraki, Japan under accession numbers FERM BP-6990 and FERM BP-6991, respectively.

The seventh aspect of the present invention relates to a method for producing a polypeptide having an α-agarase activity, comprising culturing the transformant of the fifth aspect and collecting the α-agarase of the first aspect from the culture.

The eighth aspect of the present invention relates to a method for producing an agarooligosaccharide, comprising digesting agarose using the α-agarase of the first aspect and collecting an agarooligosaccharide from the resulting digest.

The ninth aspect of the present invention relates to a novel α-agarase. Such α-agarases are exemplified by an enzyme containing an amino acid sequence consisting of 591 residues from amino acid number 335 to amino acid number 925 in the amino acid sequence of SEQ ID NO: 14, or an amino acid sequence in which one or more amino acids are substituted, deleted, added and/or inserted in said amino acid sequence consisting of 591 residues, or an enzyme containing an amino acid sequence consisting of 586 residues from amino acid number 365 to amino acid number 950 in the amino acid sequence of SEQ ID NO: 15, or an amino acid sequence in which one or more amino acids are substituted, deleted, added and/or inserted in said amino acid sequence consisting of 586 residues.

The tenth aspect of the present invention relates to a gene encoding a polypeptide having an α-agarase activity, which encodes the α-agarase of the ninth aspect. Such genes are exemplified by a gene containing a nucleotide sequence consisting of 1773 bases from base number 1003 to base number 2775 in the nucleotide sequence of SEQ ID NO: 12, or a nucleotide sequence in which one or more bases are substituted, deleted, added and/or inserted in said nucleotide sequence consisting of 1773 bases, or a gene containing a nucleotide sequence consisting of 1758 bases from base number 1093 to base number 2850 in the nucleotide sequence of SEQ ID NO: 13, or a nucleotide sequence in which one or more bases are substituted, deleted, added and/or inserted in said nucleotide sequence consisting of 1758 bases.

The eleventh aspect of the present invention relates to a gene that is hybridizable to the gene of the tenth aspect under stringent conditions and encodes the α-agarase of the ninth aspect.

The twelfth aspect of the present invention relates to a recombinant DNA molecule that contains the gene of the tenth or the eleventh aspect.

The thirteenth aspect of the present invention relates to a transformant harboring the recombinant DNA molecule of the twelfth aspect.

The fourteenth aspect of the present invention relates to a method for producing a polypeptide having an α-agarase activity, comprising culturing the transformant of the thirteenth aspect and collecting the α-agarase of the ninth aspect from the culture.

The fifteenth aspect of the present invention relates to a method for producing an agarooligosaccharide, comprising digesting agarose using the α-agarase of the ninth aspect and collecting an agarooligosaccharide from the resulting digest.

DETAILED DESCRIPTION OF THE INVENTION

Figure 1:
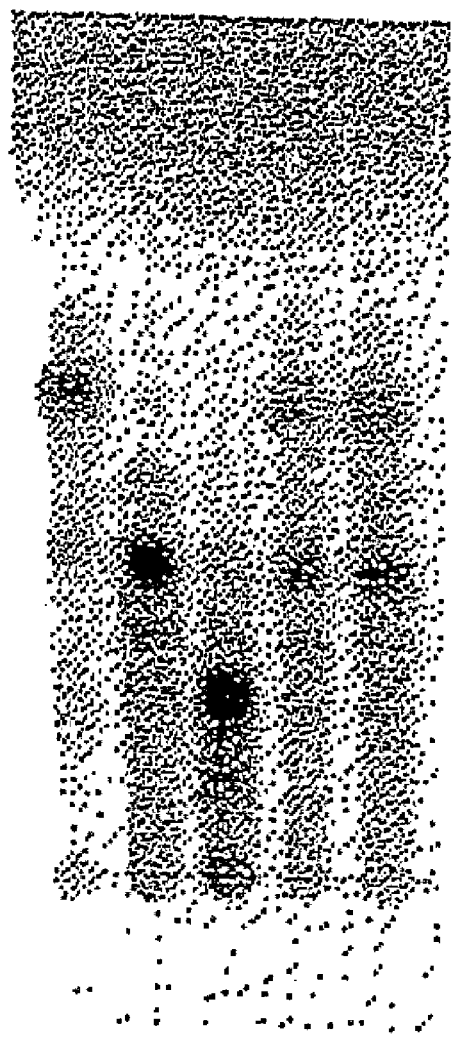
FIG. 1 illustrates digestion of agarohexaose by the α-agarase 1-7 of the present invention.

As used herein, an oligosaccharide refers to a saccharide composed of 2 or more and 10 or less monosaccharides. An agarooligosaccharide refers to an oligosaccharide that has a structure in which D-galactose and 3,6-anhydro-L-galactose are alternately linked together through α-1,3 bonds and β-1,4 bonds and has 3,6-anhydro-L-galactose at its reducing end. A polysaccharide refers to a saccharide other than monosaccharides and oligosaccharides.

The α-agarase of the present invention is an enzyme that hydrolyzes an α-1,3 bond between 3,6-anhydro-L-galactose and D-galactose. It can act on both polysaccharides such as agarose and oligosaccharides such as agarohexaose. The enzymes of the present invention are not specifically limited as long as they have such properties. Examples thereof include an α-agarase produced by a marine microorganism TKR1-7AGα (FERM BP-6990) or TKR4-3AGα (FERM BP-6991).

Agarase 1-7 produced by the microorganism TKR1-7AGα and Agarase 4-3 produced by the microorganism TKR4-3AGα are enzymes that hydrolyze α-1,3 bonds between 3,6-anhydro-L-galactose and D-galactose in polysaccharides and oligosaccharides. These enzymes act on agarose, agarohexaose and agarooligosaccharides longer than agarohexaose as well as neoagarohexaose and neoagarooligosaccharides longer than neoagarohexaose.

A method for measuring the activities of the above-mentioned two enzymes, and physical and chemical as well as enzymatic properties of the enzymes are described below.

(1) Method for Measuring Enzymatic Activity

The activity of the α-agarase of the present invention is measured by conducting an enzymatic reaction using agarose as a substrate and then quantifying the resulting agarotetraose. Specifically, the method for measuring an enzymatic activity used herein for measuring the activity of a purified enzyme preparation and an enzyme in the course of purification is as follows.

A solution containing agarose (Takara Shuzo, Code: 5003) at a concentration of 0.2% in 10 mM tris-hydrochloride (pH 7.0), 10 mM calcium chloride and 10 mM sodium chloride is prepared. 180 μl of this solution as a substrate is mixed with 20 μl of an enzyme solution. The mixture is reacted at 42° C. for 30 to 120 minutes, preferably 60 minutes, and then heated at 60° C. for 1 minute to stop the reaction. 30 μl of the reaction mixture is subjected to a TSKgel α-2500 column (inner diameter: 7.8 mm; length: 300 mm; Tosoh, Code: 18339). A peak is eluted at retention time of about 26 minutes using 70% acetonitrile solution as an eluent at a flow rate of 0.8 ml/minute. Agarotetraose produced as a result of the enzymatic reaction in the peak is quantified. One unit (1 U) is defined as the amount of the enzyme that produces 1 micromole of agarotetraose in 10 minutes.

(2) Optimal pH

An enzyme was allowed to act on agarose as a substrate in a reaction mixture prepared using an acetate buffer (pH 4.5), a malate buffer (pH 5.5), an acetate buffer (pH 6.0, 6.5) or a tris-hydrochloride buffer (pH 7.0, 7.5, 8.8). As a result, it was demonstrated that Agarase 1-7 and Agarase 4-3 exhibit their activities of digesting agarose under neutral to weakly acidic conditions and under weakly alkaline to weakly acidic conditions, respectively.

(3) Optimal Temperature

The enzyme of the present invention exhibits its enzymatic activity at a temperature of 55° C. or below. It exhibits a high activity at a temperature ranging from 30 to 48° C., and exhibits the maximal activity at about 37 to 42° C.

(4) Heat Stability

Remaining activities of enzyme preparations after treatment at 48° C., 50° C. or 60° C. for 30 seconds were measured. As a result, Agarase 1-7 exhibited 25% of its activity after treatment at 48° C., and Agarase 4-3 exhibited 22% of its activity after treatment at 50° C.

(5) Molecular Weight

The molecular weight of Agarase 1-7 was estimated to be about 95,000 as determined by SDS-polyacrylamide gel electrophoresis (SDS-PAGE) using a 10-20% polyacrylamide gradient gel.

The molecular weight of Agarase 4-3 was determined by equilibrium density-gradient centrifugation using glycerol density gradient and SDS-PAGE. As a result, the molecular weight of Agarase 4-3 was estimated to be about 85,000.

(6) Amino Acid Sequencing by Edman Degradation Method

The N-terminal amino acid sequences of Agarase 1-7 and Agarase 4-3 as determined by Edman degradation method were Asp-Thr-Leu-Ser-Val-Glu-Ala-Glu-Met-Phe and Gly-Asp-Ile-Val-Ile-Glu-Leu-Glu-Asp-Phe-Asp-Ala-Thr-Gly-Thr-Thr-Gly-Arg-Val-Ala, respectively. The N-terminal amino acid sequences of Agarase 1-7 and Agarase 4-3 are shown in SEQ ID NOS: 1 and 2, respectively.

As described below, both of a gene encoding Agarase 1-7 and a gene encoding Agarase 4-3 were isolated. Also, amino acid sequences encoded by these genes were determined. Amino acid sequences encoded by the Agarase 1-7 gene and the Agarase 4-3 gene are shown in SEQ ID NOS: 14 and 15, respectively. Both of a polypeptide consisting of 749 amino acids from amino acid number 177 to amino acid number 925 in the amino acid sequence of SEQ ID NO:14 and a polypeptide consisting of 767 amino acids from amino acid number 184 to amino acid number 950 in the amino acid sequence of SEQ ID NO:15 exhibit the activities of the α-agarase of the present invention.

Furthermore, each of the following polypeptides also exhibits an activity of the α-agarase of the present invention: a polypeptide consisting of 725 amino acids from amino acid number 201 to amino acid number 925 in the amino acid sequence of SEQ ID NO: 14; a polypeptide consisting of 591 amino acids from amino acid number 335 to amino acid number 925 in the amino acid sequence of SEQ ID NO: 14; a polypeptide consisting of 700 amino acids from amino acid number 251 to amino acid number 950 in the amino acid sequence of SEQ ID NO: 15; and a polypeptide consisting of 586 amino acids from amino acid number 365 to amino acid number 950 in the amino acid sequence of SEQ ID NO: 15.

As described below, the α-agarase of the present invention can be produced by genetic engineering using the gene for the α-agarase. If *Escherichia coli*, *Bacillus subtilis* or the like, which is widely used for production of proteins by genetic engineering, is used as a host, it is considered that the possibility of arising the following problems becomes higher as the molecular weight of the foreign protein to be expressed becomes higher:

(1) when the host is changed to another, the expressed protein may form an inclusion body and be insolubilized;

(2) the expression level may be reduced due to the preference of the host for amino acid codons;

(3) if the molecular weight of the protein to be expressed is higher than that of a protein normally contained in the host, the protein may become unstable, the expression level may be low, and the protein may be degraded in some cases; and (4) the protein may be inactivated being subjected to other modifications.

Thus, it is important to determine the minimal polypeptide portion required for exhibiting the activity of interest of the protein to be produced.

It is considered that the minimal portions for exhibiting the α-agarase activities for the agarases of the present invention, Agarase 1-7 and Agarase 4-3, are a polypeptide consisting of 591 amino acids from amino acid number 335 to amino acid number 925 in the amino acid sequence of SEQ ID NO: 14, and a polypeptide consisting of 586 amino acids from amino acid number 365 to amino acid number 950 in the amino acid sequence of SEQ ID NO: 15, respectively.

The α-agarase of the present invention can be purified from a culture obtained by culturing a microorganism TKR1-7AGα (FERM BP-6990) or a microorganism TKR4-3AGα (FERM BP-6991). TKR1-7AGα and TKR4-3AGα were isolated from seawater as bacteria that assimilate agar. They have the following microbiological properties.

Microbiological Properties:

(1) Morphology 100 ml of artificial seawater (product name: Jamarine S; Jamarine Laboratory) was prepared. 0.3 g of peptone (DIFCO, Code: 0123-17-3) and 0.02 g of yeast extract (DIFCO, Code: 0127-17-9) were added thereto. The pH was then adjusted to 8.0 with 3M sodium carbonate. The resulting mixture was transferred into a 500-ml Erlenmeyer flask. 0.1 g of agar (Nacalai Tesque, Code: 010-28) was added thereto. After sterilization in an autoclave, one of the above-mentioned microorganisms was inoculated into the mixture, and cultured at 25° C. at 120 rpm overnight. The cells of both TKR1-7AGα and TKR4-3AGα grown in the cultures were bacillary and motile.

(2) Growth 100 ml of artificial seawater (product name: Jamarine S; Jamarine Laboratory) was prepared. 0.3 g of peptone and 0.02 g of yeast extract were added thereto. The pH was then adjusted to 8.0 with 3M sodium carbonate. 1.5 g of agar (Nacalai Tesque, Code: 010-28) was added thereto. The mixture was autoclaved to prepare plates. When the above-mentioned microorganisms were inoculated onto the plates, it was demonstrated that:

(a) they grow well at 23 to 30° C.; and (b) the agar gel is liquefied as the cells grow.

100 ml of artificial seawater (product name: Jamarine S; Jamarine Laboratory) was prepared. 0.3 g of peptone and 0.02 g of yeast extract were added thereto. The pH was then adjusted to a varying value with 3M sodium carbonate. The resulting mixture was transferred into a 500-ml Erlenmeyer flask. 0.1 g of agar was added thereto. After sterilization in an autoclave, one of the above-mentioned microorganisms was inoculated into the mixture. Then, it was demonstrated that:

(c) they grow well at pH 7.0 to 8.5.

TKR1-7AGα and TKR4-3AGα were deposited under Budapest Treaty on Jan. 26, 1999 (the date of the original deposit) at the National Institute of Bioscience and Human-Technology, Agency of Industrial Science and Technology, Ministry of International Trade and Industry under accession numbers FERM BP-6990 and FERM BP-6991, respectively.

Information on the taxonomic position of each of the above-mentioned microorganisms can be obtained by analyzing the nucleotide sequence of the gene encoding 16S ribosomal RNA of which the nucleotide sequence is known to be specific for each microbial strain. Specifically, chromosomal DNAs are extracted from the microbial strains TKR1-7AGα and TKR4-3AGα. PCRs are carried out using primers that can be used to amplify a region of the gene or a portion thereof. Nucleotide sequences of the amplified DNA fragments are determined. Homology search utilizing GenBank database is conducted against the determined sequences. Then, microorganisms that have similar nucleotide sequences in the region, i.e., taxonomically close microorganisms, can be known.

DNA fragments derived from 16S ribosomal RNA genes in the microorganisms TKR1-7AGα and TKR4-3AGα were amplified according to a method as described in Bulletin of Japanese Society of Microbial Ecology, 10:31-42 (1995). Primers 27f and 1492r described in the literature were used for the PCRs (nucleotide sequences of the primers 27f and 1492r are shown in SEQ ID NOS:16 and 17). The nucleotide sequences of the resulting amplified DNA fragments were analyzed. As a result, the following microorganisms each having a homology of about 95% in the above-mentioned region with one of the microorganisms producing the α-agarase of the present invention were found:

TKR1-7AGα: Colwellia like bacterium;

TKR4-3AGα: Marine psychrophile IC079.

A medium containing a nitrogen source, an inorganic substance and the like that can be utilized by each of the microorganisms as well as agar, agarose or the like as a carbon source can be used as a medium for culturing the microorganism. Commercially available agar and agarose can be used. Examples of nitrogen sources include meat extract, yeast extract, casein hydrolysate, tryptone, peptone and the like. Yeast extract and peptone are preferably used. Such a nitrogen source can also be used as a carbon source in addition to agar or agarose. Furthermore, sodium chloride, iron citrate, magnesium chloride, sodium sulfate, calcium chloride, potassium chloride, sodium carbonate, sodium bicarbonate, potassium bromide, strontium chloride, sodium borate, sodium silicate, sodium fluoride, ammonium nitrate, disodium hydrogenphosphate and the like can be used in combination as salts.

In particular, a medium prepared by adding peptone, yeast extract and agar or agarose to a medium consisting of artificial seawater Jamarine S can be preferably used. It is preferable to add agar or agarose at a concentration of 0.1 to 2.0%. A solid or liquid medium can be prepared by appropriately changing the concentration of agar or agarose. Liquid culture using a concentration of 0.1 to 0.3% is preferable for the purpose of production of enzyme, whereas solid culture using a concentration of 1.2 to 2.0% is preferable for the purpose of preservation of cells. If low melting point agarose is used for liquid culture, it can be used at a concentration of 0.1 to 1.0%.

Although culture conditions vary more or less depending on the composition of the medium, the cultivation temperature is 23 to 30° C., preferably 25° C., the pH of the medium is 7.0 to 8.5, preferably 7.2 to 8.2, and the cultivation time is 12 to 48 hours, preferably 24 to 36 hours.

The α-agarase of the present invention produced during cultivation as described above is secreted outside the cells. Then, the cells are removed after cultivation by means of centrifugation, filtration or the like to obtain a culture supernatant.

The resulting culture supernatant can be concentrated using vacuum concentration or ultrafiltration to prepare a liquid enzyme. Alternatively, the culture supernatant can be converted to a powdery enzyme by lyophilization, spray-drying or the like to prepare a crude enzyme preparation. The α-agarase of the present invention can be partially purified by a conventional purification method such as salting out with ammonium sulfate or solvent precipitation. Furthermore, a purified enzyme preparation which results in a single band upon electrophoresis can be obtained using known purification procedures such as column chromatographies (e.g., anion-exchange column and gel filtration column) in combination.

Agarooligosaccharides such as agarobiose, agarotetraose and agarohexaose can be produced by reacting the thus-obtained culture or the α-agarase of the present invention in a varying degree of purification with a polysaccharide contained in red algae such as agar or agarose as a substrate.

Agarose is a polysaccharide that has a structure in which D-galactose and 3,6-anhydro-L-galactose are alternately linked together through α-1,3 bonds and β-1,4 bonds. β-agarase is an enzyme that hydrolyzes β-1,4 bonds in agarose. Oligosaccharides having D-galactose at their reducing ends generated by the action of this enzyme are called as neoagarooligosaccharides, which do not exhibit physiological activities such as those observed for agarooligosaccharides. If an α-agarase that cleaves α-1,3 bonds in agarose is used, agarooligosaccharides having 3,6-anhydro-L-galactose at their reducing ends can be produced. Two enzymes derived from Alteromonas agarlyticus strain GJ1B and a bacterium of genus *Vibrio* (strain JT0107-L4) are known as α-agarases. However, the α-agarase produced by Alteromonas agarlyticus strain GJ1B cannot act on agarohexaose or shorter oligosaccharides, whereas the α-agarase derived from the bacterium of genus *Vibrio* cannot digest agarose. Thus, it was impossible to efficiently produce agarobiose or agarotetraose from agarose a raw material using a known α-agarase.

The α-agarase of the present invention is an enzyme that acts on agarose, agarohexaose and agarooligosaccharides longer than agarohexaose as seen from the above-mentioned physical and chemical properties. Thus, it acts on agarose to produce agarooligosaccharides. Furthermore, it can cleave the single α-1,3 bond in agarohexaose generated as a result of the action. In other words, by allowing the α-agarase of the present invention to act on agarose, it is possible to obtain agarobiose and agarotetraose, a disaccharide and a tetrasaccharide which have been scarcely produced according to conventional methods, in large quantities.

Substrate specificities of the known α-agarases and the α-agarase of the present invention are shown in Table 1. In the table, the marks + and − represent the ability and inability of the enzyme to digest the substrate, respectively.

TABLE 1

| Substrate | Alteromonas agarlyticus GJ1B | Bacterium of genus *Vibrio* (JT0107-L4) | Agarase 1-7 Agarase 4-3 |
|---|---|---|---|
| Agarose | + | − | + |
| Agarohexaose | − | + | + |
| Agarotetraose | − | + | − |

The α-agarase of the present invention acts on agarohexaose to generate agarobiose and agarotetraose.

The agarooligosaccharides produced using the α-agarase of the present invention contain agarobiose and agarotetraose. The agarooligosaccharides may contain agarohexaose or agarooligosaccharides longer than agarohexaose as long as the existence does not interfere with the purpose of use. Agar, agarose, or oligosaccharides derived from agar or agarose may be used as a raw material for the production of agarobiose, agarotetraose and agarohexaose using the α-agarase of the present invention. The conditions used for the action of the α-agarase are not specifically limited as long as the enzyme exhibits its activity under the conditions used. For example, it is preferable to allow Agarase 1-7 to act under neutral to weakly acidic conditions, to allow Agarase 4-3 to act under weakly alkaline to weakly acidic conditions, and to allow both of the enzymes to act at 37 to 42° C. The composition of the reaction mixture is not specifically limited as long as it is suitable for the action of the enzyme.

As described above, the oligosaccharides produced using the α-agarase of the present invention are mainly hexasaccharides or shorter oligosaccharides with low degrees of polymerization. However, it is possible to optionally produce oligosaccharides with different degrees of polymerization by appropriately selecting the reaction conditions or the like. It is also possible to obtain agarobiose, agarotetraose and agarohexaose independently by separating and purifying the thus-obtained oligosaccharides.

The α-agarase gene of the present invention is a gene that encodes a polypeptide having the above-mentioned α-agarase activity. Thus, it refers to a nucleic acid that contains a nucleotide sequence encoding an amino acid sequence for a polypeptide having an α-agarase activity. Examples of the α-agarase genes of the present invention include a gene that contains a nucleotide sequence encoding Agarase 1-7 derived from the microorganism TKR1-7AGα (FERM BP-6990) and a gene that contains a nucleotide sequence encoding Agarase 4-3 derived from the microorganism TKR4-3AGα (FERM BP-6991). Genes encoding Agarase 1-7 and Agarase 4-3 are exemplified by a gene having a nucleotide sequence encoding a polypeptide consisting of 749 amino acid residues from amino acid number 177 to amino acid number 925 in SEQ ID NO:14, and a gene having a nucleotide sequence encoding a polypeptide consisting of 767 amino acid residues from amino acid number 184 to amino acid number 950 in SEQ ID NO:15.

In addition, the α-agarase genes of the present invention are exemplified by a gene encoding a polypeptide consisting of 725 amino acid residues from amino acid number 201 to amino acid number 925 in SEQ ID NO: 14; a gene having a nucleotide sequence encoding a polypeptide consisting of 591 amino acid residues from amino acid number 335 to amino acid number 925 in SEQ ID NO: 14; a gene encoding a polypeptide consisting of 700 amino acid residues from amino acid number 251 to amino acid number 950 in SEQ ID NO: 15; and a gene having a nucleotide sequence encoding a polypeptide consisting of 586 amino acid residues from amino acid number 365 to amino acid number 950 in SEQ ID NO: 15.

The α-agarase genes of the present invention also include a nucleic acid that contains a nucleotide sequence encoding a polypeptide that has an amino acid sequence in which one or more amino acids are substituted, deleted, added and/or inserted in the above-mentioned amino acid sequence and has an α-agarase activity.

Also, the genes of the present invention include a gene having a nucleotide sequence consisting of 2247 bases from base number 529 to base number 2775 in SEQ ID NO:12, and a gene having a nucleotide sequence consisting of 2301 bases from base number 550 to base number 2850 in SEQ ID NO:13.

The present invention also encompasses a gene having a nucleotide sequence consisting of 2175 bases from base number 601 to base number 2775 in SEQ ID NO: 12, a gene having a nucleotide sequence consisting of 1773 bases from base number 1003 to base number 2775 in SEQ ID NO: 12; a gene having a nucleotide sequence consisting of 2100 bases from base number 751 to base number 2850 in SEQ ID NO: 13; and a gene having a nucleotide sequence consisting of 1758 bases from base number 1093 to base number 2850 in SEQ ID NO: 13.

Furthermore, the genes of the present invention also include a nucleic acid containing a nucleotide sequence that has a nucleotide sequence in which one or more bases are substituted, deleted, added and/or inserted in the above-mentioned nucleotide sequence and encodes a polypeptide having an α-agarase activity.

Furthermore, the genes of the present invention include a nucleic acid containing a nucleotide sequence that hybridizes to the above-mentioned gene under stringent conditions and encodes a polypeptide having an α-agarase activity. Hybridization can be carried out according to a method as described in, for example, T. Maniatis et al. (eds.), Molecular Cloning: A Laboratory Manual 2nd ed., 1989, Cold Spring Harbor Laboratory. The stringent conditions are exemplified by incubation with a probe at 65° C. overnight in a solution containing 6×SSC (1×SSC: 0.15 M NaCl, 0.015 sodium citrate, pH 7.0), 0.5% SDS, 5× Denhardt's and 100 mg/ml herring sperm DNA.

A genomic DNA is prepared from a microorganism producing an α-agarase. The genomic DNA can be prepared according to an appropriate known method. For example, it can be prepared using known procedures such as lysozyme treatment, protease treatment, RNase treatment, phenol treatment and ethanol precipitation in combination. The thus-obtained genomic DNA is degraded by appropriate known means such as sonication or digestion with a restriction enzyme. The resulting DNA fragments are incorporated into a vector (e.g., a plasmid vector) according to a conventional method to construct recombinant DNA molecules. The recombinant DNA molecules are then introduced into an appropriate host (e.g., $Escherichia\ coli$) to obtain transformants. Procedures for construction of recombinant DNA molecules, transformation and the like can be appropriately selected depending on the vector and the host to be used from conventional methods, for example, those described in Molecular Cloning: A Laboratory Manual 2nd ed. Thus, a genomic library that contains a transformant harboring an α-agarase gene is obtained.

Next, the genomic library is screened to select the transformant harboring the α-agarase gene. Examples of screening methods are as follows.

(1) Screening Using Expression of α-agarase Activity as Index

A genomic library is grown on agar plates. A transformant harboring an α-agarase gene expresses a polypeptide having an α-agarase activity. The polypeptide lyses agar gel by the action of its α-agarase activity. Accordingly, a colony or a plaque that lyses agar gel in an agar plate is selected.

(2) Screening Using Antibody

A crude, partially purified or purified enzyme preparation of an α-agarase is prepared as described above. An anti-α-agarase antibody is prepared using the preparation as an antigen according to a conventional method.

A genomic library is grown on plates. Grown colonies or plaques are transferred onto nylon or nitrocellulose filters. Expressed recombinant proteins are transferred onto the filters along with the colonies or plaques. The recombinant proteins on the filters are reacted with the anti-α-agarase antibody to identify a clone reactive with the antibody.

The clone reactive with the antibody can be identified according to a known method, for example, by reacting a peroxidase-conjugated secondary antibody with the filters which have been reacted with the anti-α-agarase antibody, incubating the filter with a chromogenic substrate and then detecting developed color.

If an expression vector that results in high expression of a gene in a DNA incorporated in the vector is used for the construction of the genomic library to be used in the method (1) or (2) as described above, a transformant harboring the gene of interest can be readily selected.

(3) Screening by Hybridization Using DNA Probe

A genomic library is grown on plates. Grown colonies or plaques are transferred onto nylon or nitrocellulose filters. DNAs are immobilized onto the filters by denaturation. The DNAs on the filters are hybridized to a labeled probe according to a conventional method to identify a clone that hybridizes to the probe.

Probes used for this screening include an oligonucleotide prepared based on information on the amino acid sequence of the α-agarase as described above, an oligonucleotide prepared based on information on another amino acid sequence, and a PCR fragment amplified using primers prepared based on information on such an amino acid sequence. Examples of labels used for the probes include, but are not limited to, a radioisotopic label, a fluorescent label, a digoxigenin label and a biotin label.

A genomic library enriched for transformants harboring an α-agarase gene prepared as follows may be used as a genomic library to be used for the screening.

A genomic DNA is prepared from a microorganism producing an α-agarase, digested with an appropriate restriction enzyme, separated by agarose gel electrophoresis and then blotted onto a nylon or nitrocellulose filter according to a conventional method. The DNAs on the filter are hybridized to the above-mentioned labeled probe according to a conventional method to detect a DNA fragment that hybridizes to the probe. DNA fragments corresponding to the signal are extracted and purified from the agarose gel.

The thus-obtained DNA fragments are incorporated into a vector (e.g., a plasmid vector) according to a conventional method to construct recombinant DNA molecules. The recombinant DNA molecules are then introduced into an appropriate host (e.g., $Escherichia\ coli$) to obtain transformants. A transformation method suitable for the vector to be used can be selected from conventional methods, for example, those described in Molecular Cloning: A Laboratory Manual 2nd ed. Thus, a genomic library enriched for transformants harboring an α-agarase gene is obtained.

A screening can be carried out more efficiently by using such a genomic library.

(4) In vitro Cloning Using PCR

The gene of interest is cloned by screening transformants in the methods (1) to (3) as described above. By using a PCR, cloning can be carried out in vitro without utilizing transformants.

A genomic DNA is prepared from a microorganism producing an α-agarase. The genomic DNA is degraded by appropriate known means such as sonication or digestion with a restriction enzyme. Linkers are ligated to the thus-obtained DNA fragments according to a conventional method.

A PCR is carried out using an oligonucleotide prepared based on information on an amino acid sequence of an α-agarase and an oligonucleotide that hybridizes to the linker as primers as well as the genomic library as a template. The resulting amplification product is incorporated into a vector (e.g., a plasmid vector) according to a conventional method.

The nucleotide sequence of the α-agarase gene in the transformant harboring the α-agarase gene obtained as described above in (1) to (3) or the recombinant DNA molecule containing the α-agarase gene obtained as described above in (4) can be determined according to a known method. If the clone does not encode the entire α-agarase polypeptide, the entire open reading frame for the α-agarase is revealed by repeating a procedure comprising preparing a new probe based on the determined nucleotide sequence and screening a genomic library using the probe to obtain a new clone. A clone that contains the entire open reading frame encoding the α-agarase can be made based on the thus-obtained information, for example.

A polypeptide having an α-agarase activity can be produced in large quantities by genetic engineering by connecting the gene encoding the α-agarase obtained as described above with an appropriate expression vector.

A method for obtaining a gene for Agarase 1-7 is described below in brief.

Cells obtained by culturing TKR1-7AGα are lysed using lysozyme, and then subjected to removal of proteins, ethanol precipitation and the like to obtain a genomic DNA. The genomic DNA is partially digested with a restriction enzyme BamHI. The resulting DNA fragments are inserted into a plasmid vector (ampicillin resistant) to construct a plasmid library. The plasmid library is used to transform *Escherichia coli*. Transformants are grown on LB agar medium containing 1.5% (w/v) agar and 50 µg/ml ampicillin and cultured at 37° C. for 5 days. After cultivation, colonies for which degradation of surrounding agar is observed are isolated, inoculated into LB medium containing ampicillin and cultured. An α-agarase activity is determined for a crude extract prepared from the cells. A plasmid DNA was extracted according to a conventional method from a transformant for which an α-agarase activity was observed. The length of a DNA inserted in the plasmid DNA was determined to be about 8 kb. This recombinant plasmid is designated as pAA1. *Escherichia coli* transformed with the plasmid is designated and indicated as *Escherichia coli* JM109/pAA1, and deposited under Budapest Treaty on May 26, 1999 (the date of the original deposit) at the National Institute of Bioscience and Human-Technology, Agency of Industrial Science and Technology, Ministry of International Trade and Industry, 1-3, Higashi 1-chome, Tsukuba-shi, Ibaraki, Japan under accession number FERM BP-6992.

Analysis of the nucleotide sequence of the DNA fragment inserted in the plasmid pAA1 revealed that it contains an open reading frame (ORF) that encodes a polypeptide consisting of 925 amino acids as a region encoding an α-agarase. The nucleotide sequence of the open reading frame and the amino acid sequence encoded by the open reading frame are shown in SEQ ID NOS: 12 and 14, respectively. Thus, the amino acid sequence of SEQ ID NO: 14 is an example of the agarase of the present invention. Comparison of this amino acid sequence with the previously determined N-terminal amino acid sequence of Agarase 1-7, P1, shows that Agarase 1-7 is a polypeptide consisting of an amino acid sequence from amino acid number 28 to amino acid number 925 in the amino acid sequence of SEQ ID NO:14, and that the amino acid sequence is encoded by a nucleotide sequence from base number 82 to base number 2778 (including the termination codon) in the nucleotide sequence of SEQ ID NO:12. The amino acid sequence consisting of the amino acids 1 to 27 in the amino acid sequence of the SEQ ID NO: 14 is considered to be a signal sequence. Furthermore, a polypeptide having an amino acid sequence consisting of 749 residues from amino acid number 177 to amino acid number 925 in the amino acid sequence of SEQ ID NO:14 also has an activity of the α-agarase of the present invention.

A method for obtaining a gene for α-Agarase 4-3 is described below in brief. Mixed primers 3 and 4 were prepared based on the N-terminal amino acid sequence of Agarase 4-3, P2, represented by SEQ ID NO: 2. The sequences of the mixed primers 3 and 4 are shown in SEQ ID NOS: 6 and 7, respectively.

A chromosomal DNA prepared from TKR4-3AGα as described above for α-Agarase 1-7 was completely digested with a restriction enzyme BamHI. BamHI linkers were ligated to the termini of the digested DNA. A PCR was carried out using the resulting DNA as a template as well as the mixed primer 3 and a primer C1 attached to LA PCR in vitro cloning kit (Takara Shuzo).

Next, a PCR was carried out using the thus-obtained product of the primary PCR as a template as well as the mixed primer 4 and a primer C2 attached to LA PCR in vitro cloning kit (Takara Shuzo). As a result, an amplification product of about 2 kb was observed. This DNA fragment was designated as 4-3N.

The nucleotide sequences of the terminal regions of the amplified fragment were analyzed. Primers 6 and 7 of which the nucleotide sequences are shown in SEQ ID NOS: 8 and 9, respectively, were prepared based on a nucleotide sequence corresponding to a region that encodes the N-terminal portion of the agarase. Similarly, primers 8 and 9 of which the nucleotide sequences are shown in SEQ ID NOS: 10 and 11, respectively, were prepared based on a nucleotide sequence corresponding to the C-terminal portion of the agarase.

When a PCR was carried out as described above for 4-3N except that primers 6 and 7 were used in place of the mixed primers 3 and 4, a DNA fragment of about 1.0 kb, 4-3UN, was obtained. Similarly, when a PCR was carried out using primers 8 and 9, a DNA fragment of about 2.0 kb, 4-3C, was obtained. Analysis of the nucleotide sequences of the fragments 4-3UN and 4-3C, while taking the previously determined nucleotide sequence of 4-3N in consideration, revealed an open reading frame that encodes a polypeptide consisting of 951 amino acids. The nucleotide sequence of the open reading frame and the amino acid sequence encoded by the nucleotide sequence of the open reading frame are shown in SEQ ID NOS: 13 and 15, respectively. In 4-3UN, a nucleotide sequence for the amino acid sequence P2, an upstream nucleotide sequence encoding 183 amino acids, and a further upstream SD-like sequence were found.

Thus, the amino acid sequence of SEQ ID NO: 15 is an example of the agarase of the present invention. Comparison of this amino acid sequence with the previously determined N-terminal amino acid sequence of Agarase 4-3 shows that Agarase 4-3 is a polypeptide consisting of an amino acid sequence from amino acid number 184 to amino acid number 951 in the amino acid sequence of SEQ ID NO:15, and that the amino acid sequence is encoded by a nucleotide sequence from base number 550 to base number 2856 (including the termination codon) in the nucleotide sequence of SEQ ID NO:13.

The amino acid sequences of Agarase 1-7 and Agarase 4-3 obtained as described above as well as the nucleotide sequences of the genes encoding these enzymes have no homology with the amino acid sequences of β-agarases, which are known agarose-digesting enzymes that cleave agarose in a different manner from the agarase of the present invention, and the nucleotide sequences of the genes encoding the enzymes. Thus, these sequences are considered to be absolutely novel.

A recombinant DNA molecule can be constructed by connecting a gene encoding the α-agarase of the present invention (e.g., the gene encoding Agarase 1-7 or Agarase 4-3) to an appropriate vector. Furthermore, a transformant can be made by introducing the recombinant DNA molecule into an appropriate host. The α-agarase of the present invention is produced in a culture obtained by culturing the transformant. Thus, it is possible to produce the α-agarase of the present invention (e.g., Agarase 1-7 or Agarase 4-3) in large quantities using the transformant.

A mutated α-agarase can be produced by introducing a mutation into a gene encoding an α-agarase according to a known method. Examples of the methods for introducing a mutation that can be used include, but are not limited to, the oligonucleotide double amber method (Hashimoto-Gotoh, T. et al., Gene, 152:271-275 (1995)), the gapped duplex method (Kramer, W. et al., Nucl. Acids Res., 12:9441 (1984); Kramer, W. et al., Methods in Enzymology, 154:350 (1987)) and the Kunkel method (Kunkel, T. A., Proc. Natl. Acad. Sci. USA, 82:488 (1985); Kunkel, T. A., Methods in Enzymology, 154:367 (1987)).

The α-agarase genes having nucleotide sequences of SEQ ID NOS: 12 and 13 were deleted from the 5'-termini. The polypeptides encoded by the resulting deleted genes were expressed. The α-agarase activities were then determined for the polypeptides. As a result, it was demonstrated that each of the following genes encodes a polypeptide having an activity of the α-agarase of the present invention: a gene having a nucleotide sequence consisting of 2247 bases from base number 529 to base number 2775 in SEQ ID NO: 12; a gene having a nucleotide sequence consisting of 2175 bases from base number 601 to base number 2775 in SEQ ID NO: 12; a gene having a nucleotide sequence consisting of 1773 bases from base number 1003 to base number 2775 in SEQ ID NO: 12; a gene having a nucleotide sequence consisting of 2301 bases from base number 550 to base number 2850 in SEQ ID NO: 13; a gene having a nucleotide sequence consisting of 2100 bases from base number 751 to base number 2850 in SEQ ID NO: 13; and a gene having a nucleotide sequence consisting of 1758 bases from base number 1093 to base number 2850 in SEQ ID NO: 13.

The α-agarase of interest can be secreted outside a transformant by expressing a gene that encodes a polypeptide in which a signal sequence is added at the N-terminus of the α-agarase to be expressed. The signal sequence is not limited to specific one, and exemplified by the signal sequence for α-Agarase 1-7 represented by amino acid numbers 1 to 27 in SEQ ID NO: 14. This signal sequence is encoded by a nucleotide sequence from base number 1 to base number 81 in SEQ ID NO: 12.

Examples of vectors that can be used for constructing the recombinant DNA molecules include, but are not limited to, plasmid vectors, phage vectors and virus vectors. An appropriate vector may be selected depending on the purpose for which the recombinant DNA is used. In case where a recombinant DNA molecule is constructed in order to produce an α-agarase, a vector that contains a promoter and/or other regions for expression control is preferable. Examples of such plasmid vectors include, but are not limited to, pKF19k, pT7BlueT and pET16b. Hosts that can be used for making transformants include, but are not limited to, microorganisms such as bacteria, yeasts and filamentous fungi, as well as cultured cells of mammals, fishes, insects and the like. A recombinant DNA molecule constructed using a vector suitable for the host is used for making a transformant.

A method for producing Agarase 1-7 by genetic engineering is described below in brief.

A DNA fragment containing a nucleotide sequence that encodes a polypeptide having, for example, an amino acid sequence starting from amino acid number 28 or 177 in SEQ ID NO: 14 is amplified by a PCR using the plasmid pAA1 which encodes the α-Agarase 1-7 gene as a template to construct a plasmid in which the amplified fragment is inserted into an appropriate plasmid vector (e.g., pKF19k (Takara Shuzo), pT7BlueT (Takara Shuzo) or pET16b (Takara Shuzo)). Escherichia coli (e.g., Escherichia coli JM109 or BL21 (DE3)pLysS) transformed with such a plasmid is cultured in an appropriate liquid medium. Induction is carried out using IPTG or the like, if necessary. The polypeptide encoded by the DNA fragment inserted in the plasmid is expressed. The α-agarase activity expressed by such a transformant in a unit volume of culture is usually higher than that observed for a culture of TKR1-7AGα.

For Agarase 4-3, a transformant expressing the α-agarase can be made by genetic engineering as described above for Agarase 1-7 after amplifying a DNA fragment containing a nucleotide sequence that encodes, for example, a polypeptide having an amino acid sequence starting from amino acid number 184 in SEQ ID NO: 15 by a PCR using a chromosomal DNA from the microorganism TKR4-3α as a template. The resulting transformant expresses an α-agarase activity, and the activity in a unit volume of culture is usually higher than that observed for a culture of TKR4-3AGα.

The α-agarase of the present invention produced by genetic engineering as described above can be partially purified by a conventional purification method such as salting out with ammonium sulfate or solvent precipitation. Furthermore, a purified enzyme preparation which results in a single band upon electrophoresis can be obtained using known purification procedures such as column chromatographies (e.g., anion-exchange column and gel filtration column) in combination.

Agarooligosaccharides such as agarobiose, agarotetraose and agarohexaose can be produced by reacting the thus-obtained recombinant α-agarase of the present invention in a varying degree of purification with a polysaccharide contained in red algae such as agar or agarose as a substrate.

The following Examples illustrate the present invention in more detail, but are not to be construed to limit the scope thereof.

EXAMPLE 1

Production of α-agarase from TKR1-7AGα

Upon purification of the α-agarase of the present invention, the enzymatic activity was measured by conducting an enzymatic reaction using agarose L03 (Takara Shuzo, Code: 5003) as a substrate and then quantifying the resulting agarotetraose using high-performance liquid chromatography. The procedure is described in detail below.

A solution containing agarose L03 at a concentration of 0.2% in 10 mM tris-hydrochloride (pH 7.0), 10 mM calcium chloride and 10 mM sodium chloride was prepared. 180 μl of this solution was mixed with 20 μl of an enzyme solution. The mixture was reacted at 42° C. for 30 to 120 minutes, preferably 60 minutes, and then heated at 60° C. for 1 minute to stop the reaction. 30 μl of the reaction mixture was subjected to a TSKgel α-2500 column (inner diameter: 7.8 mm; length: 300 mm; Tosoh, Code: 18339). A peak was eluted at retention time of about 26 minutes using 70% acetonitrile solution as an eluent at a flow rate of 0.8 ml/minute. Agarotetraose produced as a result of the enzymatic reaction in the peak was quantified. One unit (1 U) of the α-agarase of the present invention is defined as the amount of the enzyme that produces 1 micromole of agarotetraose in 10 minutes.

100 ml of artificial seawater (product name: Jamarine S; Jamarine Laboratory) was prepared. Peptone (DIFCO, Code: 0123-17-3) and yeast extract (DIFCO, Code: 0127-17-9) were added thereto at concentrations of 0.3% and 0.02%, respectively. The pH was then adjusted to 8.0 using 3M sodium carbonate. The resulting mixture was transferred into a 500-ml Erlenmeyer flask. 0.1 g of agar (Nacalai Tesque, Code: 010-28) was added thereto. After sterilization in an autoclave, the microorganism TKR1-7AGα was inoculated into the mixture, and cultured at 25° C. at 120 rpm overnight. The resulting culture was used as a preculture.

The main cultivation was conducted as follows. 3 l of the above-mentioned medium was prepared in a 5- jar fermentor vessel and sterilized in an autoclave. 30 ml of the preculture was inoculated into the medium and cultured at 25° C. at 250 rpm for 24 hours. The culture was then centrifuged at 8,000×g for 20 minutes to collect about 3 l of a supernatant from which cells had been removed.

The following procedures were carried out at 4° C. or below.

The supernatant was placed in a dialysis membrane (Sanko Junyaku, Code: UC-36-32-100) and soaked in about 500 g of polyethylene glycol over two nights to concentrate until the volume of the internal solution became about 100 ml, and then dialyzed against Buffer A (20 mM tris-hydrochloride (pH 7.0), 10 mM calcium chloride, 10 mM sodium chloride) for desalting. The dialyzate was loaded onto a column (φ2 cm×9.5 cm) filled with 30 ml of strong anion-exchange resin Super Q (Tosoh, Code: 17227) which had been equilibrated with the Buffer A. The adsorbed α-agarase was eluted using a linear gradient of 10 mM to 150 mM calcium chloride (total elution volume: 600 ml). A fraction of about 60 ml with an α-agarase activity eluted at a calcium chloride concentration between 50 mM and 100 mM was collected.

This fraction was dialyzed against Buffer B (10 mM tris-hydrochloride (pH 7.0), 10 mM calcium chloride, 10 mM sodium chloride) for desalting, and then loaded onto a column (φ2 cm×6.3 cm) filled with 20 ml of Super Q. In this case, the adsorbed enzyme was eluted using a linear gradient of 10 mM to 1.0 M sodium chloride (total elution volume: 200 ml). A fraction of 40 ml with an α-agarase activity eluted at about 0.5 M was obtained. This fraction was dialyzed against the Buffer B, and subjected to a column (φ0.8 cm×5.7 cm) filled with 10 ml of DEAE-TOYOPEARL (Tosoh, Code: 007473). A fraction of about 20 ml with an α-agarase activity was collected using a linear gradient of 10 mM to 150 mM calcium chloride (total elution volume: 100 ml).

The fraction was then concentrated to about 1 ml using a centrifugation ultrafiltration membrane Centriprep-10 (Amicon, Code: 4304). The concentrate was subjected to gel filtration using a column (φ0.8 cm×60 cm) filled with Sephadex G-100 (Pharmacia, Code: 17-0060-01) equilibrated with the Buffer B to obtain a fraction of about 15 ml with an α-agarase activity. This fraction was subjected to a column (φ0.8 cm×10 cm) of 5 ml of QAE-TOYOPEARL (Tosoh, Code: 14026), and eluted using a linear gradient of 10 mM to 150 mM calcium chloride (total elution volume: 100 ml) to obtain an α-agarase fraction of about 4 ml.

Analysis of the thus-obtained α-agarase fraction by SDS-PAGE revealed that the enzyme of interest was purified almost to homogeneity, and that the molecular weight was about 95,000. The total activity of the thus-obtained purified α-agarase preparation was 45 U. This fraction was used as Agarase 1-7 in experiments hereinafter.

EXAMPLE 2

Production of α-agarase from TKR4-3AGα

The microorganism TKR4-3AGα was cultured as described above for the microorganism TKR1-7AGα in Example 1 to obtain about 3 l of a culture supernatant.

The culture supernatant was placed in a dialysis membrane (Sanko Junyaku, Code: UC-36-32-100) and soaked in about 500 g of polyethylene glycol over two nights to concentrate until the volume of the internal solution became about 300 ml, and then dialyzed against Buffer C (10 mM tris-hydrochloride (pH 7.0), 10 mM calcium chloride, 50 mM sodium chloride). About two thirds of the dialyzate was loaded onto a column (φ2 cm×9.5 cm) filled with 30 ml of Super Q which had been equilibrated with the Buffer C. The adsorbed α-agarase was eluted using a linear gradient of 10 mM to 80 mM calcium chloride (total elution volume: 400 ml). A fraction of about 40 ml with an α-agarase activity eluted at a calcium chloride concentration between 40 mM and 50 mM was collected.

This fraction was concentrated using Centriprep-10 and diluted with the Buffer B for desalting, and then loaded onto a column (φ1.5 cm×5.7 cm) filled with 10 ml of DEAE-TOYOPEARL. The adsorbed α-agarase was eluted using a linear gradient of 10 mM to 100 mM calcium chloride (total elution volume: 100 ml). A fraction of 9 ml with an α-agarase activity eluted at a calcium chloride concentration of about 45 mM was obtained. This fraction was concentrated using Centriprep-30 (Amicon, Code: 4306), diluted 5-fold with the Buffer B, and then subjected to a column (φ0.8 cm×4 cm) filled with 2 ml of QAE-TOYOPEARL equilibrated with the Buffer B. A fraction of α-agarase adsorbed to the column was collected using a linear gradient of 10 mM to 120 mM calcium chloride (total elution volume: 40 ml).

Analysis of the thus-obtained α-agarase fraction by SDS-PAGE revealed that the α-agarase was purified almost to homogeneity. The total activity obtained was 1.53 U. This fraction was used as Agarase 4-3 in experiments hereinafter.

EXAMPLE 3

Examination of Various Properties of Enzymes (1) Substrate Specificity and Action 10 μl of a buffer for reaction (10 mM tris-hydrochloride (pH 7.0), 10 mM calcium chloride, 10 mM sodium chloride) containing one selected from the group consisting of four types of agarooligosaccharides (agarobiose, agarotetraose, agarohexaose and agarooctaose) (each at a concentration of 2.5 mM), three types of neoagarooligosaccharides (neoagarobiose, neoagarotetraose and neoagarohexaose) (each at a concentration of 2.5 mM) and agarose L03 (at a concentration of 1%) was prepared. 10 μl of a solution of Agarase 1-7 or Agarase 4-3 was added thereto. The mixture was reacted at 42° C. for 30 minutes. The reaction products were subjected to thin-layer chromatography using a developing solvent having a composition of chloroform:methanol:acetic acid=3:3:1. After development, reaction products were confirmed by orcinol-sulfuric acid method.

As a result, it was demonstrated that both Agarase 1-7 and Agarase 4-3 cleave agarohexaose, agarooctaose, neoagarohexaose and agarose.

Figure 2:
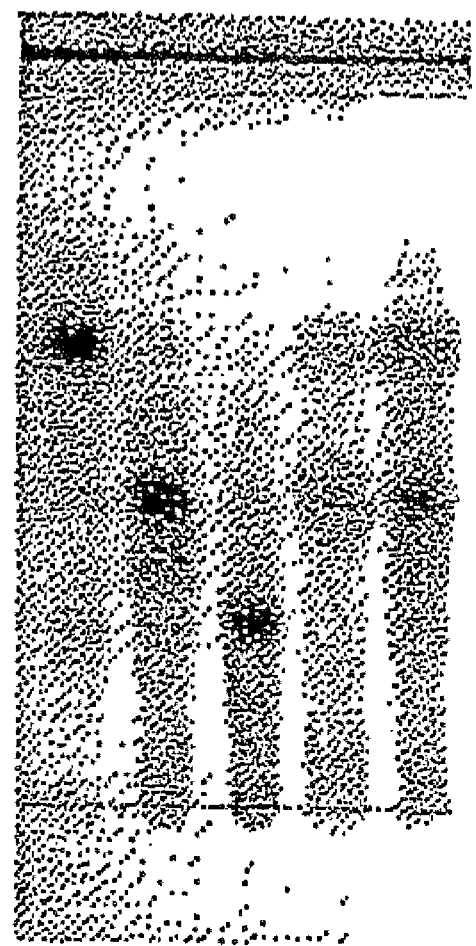
FIG. 2 illustrates digestion of agarohexaose by the α-agarase 4-3 of the present invention.

The results of thin-layer chromatography obtained when Agarase 1-7 was allowed to act on agarohexaose are shown in FIG. 1. The results of thin-layer chromatography obtained when Agarase 4-3 was allowed to act on agarohexaose are shown in FIG. 2. In FIGS. 1 and 2, the samples developed in the respective lanes are as follows: lane 1: agarobiose; lane 2: agarotetraose; lane 3: agarohexaose; lane 4: agarohexaose reacted with the agarase of the present invention; lane 5: a mixture of agarobiose and agarotetraose. As seen from these figures, the α-agarase of the present invention digests agarohexaose to generate agarobiose and agarotetraose.

(2) Identification of Product of Reaction with α-agarase

Agarase 1-7 or Agarase 4-3 was added to 2.0 ml of a solution containing agarose L03 at a concentration of 1.0% in 10 mM tris-hydrochloride (pH 7.0), 10 mM calcium chloride and 10 mM sodium chloride. The mixture was reacted at 42° C. for 60 minutes. After reaction, a portion of the reaction mixture was subjected to a gel filtration column (Tosoh, TSKgel α-2500) and chromatographed using 70% acetonitrile as an eluent at a flow rate of 0.8 ml/minute. A fraction eluted at retention time of about 26 minutes was collected and concentrated to dryness using a rotary evaporator. The weight of the product was determined to be about 4 mg.

Analysis of the fraction by nuclear magnetic resonance using JNM-EX270 FT NMR system (Nippon Denshi) confirmed that the substance which was generated from agarose by the action of each enzyme and contained in the fraction was agarotetraose. Thus, it was demonstrated that both Agarase 1-7 and Agarase 4-3 hydrolyzes the α-1,3 bond between D-galactose and 3,6-anhydro-L-galactose in a agarose molecule to generate agarooligosaccharides containing agarotetraose.

(3) Reaction pH

10 μl of a reaction mixture containing 1% agarose L03, 10 mM calcium chloride and 10 mM sodium chloride whose pH was adjusted to the following value using a buffer indicated in parentheses at a final concentration of 10 mM was prepared: 4.5 (acetate buffer); 5.5 (malate buffer); 6.0, 6.5 (acetate buffer); or 7.0, 7.5 or 8.8 (tris buffer). 10 μl of an enzyme solution was added thereto. The mixture was reacted at 42° C. for 1 hour. The reaction mixture was subjected to thin-layer chromatography and developed using chloroform:methanol:acetic acid=3:3:1 (v/v/v). Reaction products were confirmed by orcinol-sulfuric acid method. As a result, it was demonstrated that Agarase 1-7 and Agarase 4-3 exhibit their activities of digesting agarose under neutral to weakly acidic conditions and under weakly alkaline to weakly acidic conditions, respectively.

(4) Optimal Temperature

The enzymatic activities of Agarase 1-7 and Agarase 4-3 were measured at various temperatures. For each of Agarase 1-7 and Agarase 4-3, the temperature at which inactivation of the enzyme was suppressed and the reaction rapidly proceeded was 37 to 42° C.

(5) Heat Stability

A purified enzyme solution of Agarase 1-7 or Agarase 4-3 was heated at 48° C., 50° C. or 60° C. for 30 seconds. A solution containing agarose L03 at a concentration of 0.2% in 10 mM tris-hydrochloride (pH 7.0), 10 mM calcium chloride and 10 mM sodium chloride was then added to the heated solution. The mixture was reacted at 42° C. for 1 hour. The reaction was terminated by heating for 1 minute in boiling water. Reaction products were quantified according to the method for measuring an activity as described in Example 1. As a result, Agarase 1-7 exhibited 25% of its activity after treatment at 48° C., and Agarase 4-3 exhibited 22% of its activity after treatment at 50° C., defining the activity without the heat treatment as 100%.

(6) Molecular Weight

The molecular weight of Agarase 1-7 was determined by SDS-polyacrylamide gel electrophoresis. Agarase 1-7 was electrophoresed using a 10-20% polyacrylamide gradient gel containing SDS along with a molecular weight marker (Bio-Rad, myosin (m.w. 200,000), β-galactosidase (m.w. 116,250), phosphorylase b (m.w. 97,400), bovine serum albumin (m.w. 66,200), ovalbumin (m.w. 45,000), carbonic anhydrase (m.w. 31,000), trypsin inhibitor (m.w. 21,500), lysozyme (m.w. 14,400)). The molecular weight of Agarase 1-7 was about 95,000 dalton as determined based on the mobility on the gel.

The molecular weight of Agarase 4-3 was determined by equilibrium density-gradient centrifugation. Density gradient was prepared by varying the concentration of glycerol from 15% to 35% in a buffer containing 10 mM tris-HCl (pH 7.0), 10 mM calcium chloride and 50 mM sodium chloride. 4.8 ml of linear density gradients were prepared in two 5-ml centrifugation tubes such that the lowermost layer contained glycerol at a concentration of 35% and the uppermost layer contained glycerol at a concentration of 15%. 100 μl of a solution containing 15 μl of a molecular weight marker Low Range (Bio-Rad) and glycerol at a concentration of 15% in the above-mentioned buffer was overlaid onto the top of one of the tubes. 100 μl of the enzyme preparation of Agarase 4-3 was overlaid onto the other tube. These centrifugation tubes were centrifuged using a swing rotor at 45,000 rpm at 4° C. for 21 hours. After centrifugation, fractions 1 to 20 each containing 250 μl of the buffer were collected from the top to the bottom of each centrifugation tube. The respective fractions collected from the centrifugation tube to which the molecular weight marker was added were subjected to SDS-PAGE. The respective fractions collected from the centrifugation tube to which the enzyme preparation was added were subjected to SDS-PAGE and measurement of enzymatic activities. A peak of the enzymatic activity of α-agarase was detected for the fraction nos. 8-10 corresponding to molecular weight of about 65,000 to 85,000 based on the results of SDS-PAGE of the fractions containing the molecular weight marker. Based on these results as well as the results of SDS-PAGE of the fractions containing the enzyme preparation, the molecular weight of Agarase 4-3 was estimated to be about 85,000.

(7) Amino Acid Sequence Analysis by Edman Degradation Method

The amino acid sequences of α-Agarase 1-7 and α-Agarase 4-3 obtained in Examples 1 and 2 were determined by Edman degradation method. A purified enzyme preparation containing Agarase 1-7 or Agarase 4-3 corresponding to 10 pmole of the enzyme protein was subjected to SDS-PAGE using a 10-20% polyacrylamide gradient gel. After electrophoresis, the enzyme separated on the gel was blotted onto a membrane ProBlot (Applied Biosystems). A portion of the membrane to which the enzyme had been adsorbed was analyzed using a protein sequencer G1000A (Hewlett Packard). As a result, an amino acid sequence P1: Asp-Thr-Leu-Ser-Val-Glu-Ala-Glu-Met-Phe (SEQ ID NO: 1) and an amino acid sequence P2: Gly-Asp-Ile-Val-Ile-Glu-Leu-Glu-Asp-Phe-Asp-Ala-Thr-Gly-Thr-Thr-Gly-Arg-Val-Ala (SEQ ID NO:2) were determined for Agarase 1-7 and Agarase 4-3, respectively.

EXAMPLE 4

Production of Agarooligosaccharides

Agarose L03 was added to 2 ml of a buffer for reaction (10 mM tris-hydrochloride (pH 7.0), 10 mM calcium chloride, 10 mM sodium chloride) at a concentration of 1.0% (w/v). 2 U of the purified preparation of Agarase 1-7 was further added thereto. The mixture was reacted at 42° C. for 16 hours. After reaction, the reaction mixture was filtered through a 0.22-μm filter (Millipore, Code: SLGVL040S). The filtered reaction mixture was analyzed using high-performance liquid chromatography under the same conditions as those used for measuring the activity of the enzyme of the present invention in Example 1 to determine the generated agarooligosaccharides. As a result, agarobiose, agarotetraose and agarohexaose were detected in the reaction mixture. Thus, it was confirmed that the above-mentioned enzymatic reaction produces these smaller agarooligosaccharides.

EXAMPLE 5

Preparation of Chromosomal DNAs from TKR1-7AGα and TKR4-3AGα

Artificial seawater (product name: Jamarine S; Jamarine Laboratory) was prepared. Peptone (DIFCO, Code: 0123-17-3) and yeast extract (DIFCO, Code: 0127-17-9) were added thereto at concentrations of 0.3% (w/v) and 0.02% (w/v), respectively. The pH was then adjusted to 8.0 using 3M sodium carbonate. Agar (Nacalai Tesque, Code: 010-28) was added thereto at a concentration of 0.1% (w/v). The mixture was sterilized in an autoclave. 10 µl of a glycerol stock of one of the α-agarase-producing strains TKR1-7AGα and TKR4-3AGα was inoculated into 2 ml of the medium and cultured at 25° C. overnight. 1 ml of the culture was inoculated into 100 ml of the same medium and cultured at 25° C. overnight. The cells were collected by centrifugation at 8,000×g for 10 minutes. The cells were suspended in 10 ml of Buffer A (100 mM sodium chloride, 100 mM tris-hydrochloride (pH 8.0), 10 mM EDTA (pH 8.0)). 0.25 ml of a lysozyme solution (20 mg/ml) was added thereto. The mixture was incubated at 37° C. for 1 hour. 2.5 ml of the Buffer A containing SDS at a concentration of 5% was then added thereto. The resulting mixture was incubated at 60° C. for 20 minutes while shaking. 1.5 ml of a protease K solution (20 mg/ml) was added thereto. The mixture was incubated at 37° C. overnight. Almost equal volume of phenol was then added thereto, and the mixture was gently shaken at room temperature for about 10 minutes. The mixture was centrifuged at 2,000×g for 10 minutes. The supernatant was transferred into cold ethanol. A chromosomal DNA was wound using a glass bar. After repeating the procedure twice, 50 µl of an RNase solution (10 mg/ml) was added, and the mixture was incubated at 37° C. for 10 minutes. The chromosomal DNA was recovered from the solution by ethanol precipitation and suspended in 5 ml of Buffer B (140 mM sodium chloride, 20 mM tris-hydrochloride (pH 7.5), 1 mM EDTA (pH 7.5)). The suspension was dialyzed against the same buffer overnight. Then, about 1.5 mg and about 3.1 mg of chromosomal DNAs were obtained from TKR1-7AGα and TKR4-3AGα, respectively. The purity of each DNA was examined based on OD260 nm/280 nm. The value was about 1.8 in each case. The chromosomal DNAs were used for cloning as described below.

EXAMPLE 6

Cloning of α-agarase 1-7 Gene

10 µg of the chromosomal DNA from TKR1-7AGα partially digested with a restriction enzyme BamHI was subjected to electrophoresis using 1.0% low melting point agarose gel. After staining with ethidium bromide, a portion corresponding to 4 to 10 kb was excised under ultraviolet irradiation. The DNA was extracted and purified from the gel by heat-melting according to a conventional method. The recovered DNA fragments were inserted into a BamHI site in a plasmid pUC19 (Takara Shuzo) using a DNA ligation kit (Takara Shuzo). The plasmid library was used to transform *Escherichia coli* JM109. Transformants were grown on LB agar medium containing agar at a concentration of 1.5% (w/v) and ampicillin at a concentration of 50 µg/ml. After culturing at 37° C. overnight, about 1000 transformants were grown on one plate. 20 plates were further incubated at 25° C. for 4 days. As a result, degradation of surrounding agar was observed for two colonies. Each of these strains was inoculated into 2 ml of LB medium containing ampicillin and cultured at 37° C. overnight. An α-agarase activity was recognized for a crude extract prepared from the resulting cells. A plasmid DNA was extracted from each transformant according to a conventional method. The length of the inserted DNA was determined by digestion with a restriction enzyme BamHI to be about 7.2 kb for each of the transformants. These hybrid plasmids were considered to be identical each other based on the restriction enzyme digestion patterns, and designated as pAA1. *Escherichia coli* transformed with the plasmid pAA1 is designated and indicated as *Escherichia coli* JM109/pAA1, and deposited under Budapest Treaty on May 26, 1999 (the date of the original deposit) at the National Institute of Bioscience and Human-Technology, Agency of Industrial Science and Technology, Ministry of International Trade and Industry under accession number FERM BP-6992.

A mixed primer 1 represented by SEQ ID NO: 3 was designed based on the amino acid sequence of Agarase 1-7, P1, represented by SEQ ID NO:1. A PCR was carried out using this primer and a primer 2 represented by SEQ ID NO: 4 which specifically hybridizes to a pUC vector as well as pAA1 as a template.

50 ng of pAA1, 5 µl of ExTaq buffer, 8 µl of a dNTP mixture, 1 µl of the mixed primer 1, 1 µl of the primer 2 and 0.5 µl of TaKaRa ExTaq were added to a 0.5 ml tube for PCR. Sterile water was further added thereto to make the total volume to 50 µl. After the solution was overlaid with 50 µl of mineral oil, the tube was placed in an automated gene amplification instrument Thermal Cycler (Takara Shuzo). After denaturing at 94° C. for 2 minutes, a PCR of 30 cycles was performed. Each cycle consisted of denaturation at 94° C. for 1 minute, annealing of primers at 50° C. for 2 minutes and synthesis reaction at 72° C. for 3 minutes. After the PCR, the whole reaction mixture was subjected to electrophoresis on 1.0% low melting point agarose gel. An amplified DNA fragment of about 3.5 kb excised from the gel was ligated to pT7Blue (Novagen). The nucleotide sequence of this DNA fragment was determined from the N-terminal side according to the dideoxy chain terminator method using Taq DNA polymerase. A primer represented by SEQ ID NO: 5 was designed based on the sequence determined as described above. The upstream nucleotide sequence was determined using this primer. As a result, it was found that there exists a nucleotide sequence that encodes 27 amino acids upstream from the nucleotide sequence corresponding to the amino acid sequence P1 represented by SEQ ID NO: 1, there exists an SD-like sequence in the further upstream region, and pAA1 contains an open reading frame (ORF) that encodes a polypeptide consisting of a total of 925 amino acids. The nucleotide sequence of the open reading frame and the amino acid sequence encoded by the open reading frame are shown in SEQ ID NOS: 12 and 14, respectively. The N-terminal sequence of the α-agarase purified from the microorganism TKR1-7AGα, P1, matched with the sequence of the 28th to 37th amino acids in the amino acid sequence of SEQ ID NO: 13.

EXAMPLE 7

Cloning of α-Agarase 4-3 Gene

Mixed primers 3 and 4 were designed based on the sequences of the amino acid numbers 2-11 and 12-20 in the amino acid sequence of Agarase 4-3, P2, represented by SEQ ID NO: 2. These primers were used to clone a gene for Agarase 4-3 using LA PCR in vitro cloning kit (Takara Shuzo). The sequences of the mixed primers 3 and 4 are shown in SEQ ID NOS: 6 and 7, respectively.

A primary PCR was carried out as follows. The chromosomal DNA prepared from TKR4-3AGα in Example 5 was completely digested with a restriction enzyme BamHI. BamHI linkers were ligated to the termini of the digested DNA using a DNA ligation kit (Takara Shuzo). A portion of the ligation mixture was placed in a 0.5-ml tube for PCR, and 5 µl of 10×LA PCR buffer, 8 µl of a dNTP mixture, 1 µl of the mixed primer 3, 1 µl of a primer C1 attached to LA PCR in vitro cloning kit (Takara Shuzo) and 0.5 µl of TaKaRa LATaq were added thereto. Sterile water was further added thereto to make the total volume to 50 µl. After the solution was overlaid with 50 µl of mineral oil, the tube was placed in an automated gene amplification instrument Thermal Cycler (Takara Shuzo). After denaturing at 94° C. for 2 minutes, a PCR of 30 cycles was performed. Each cycle consisted of denaturation at 94° C. for 1 minute, annealing of primers at 50° C. for 2 minutes and synthesis reaction at 72° C. for 3 minutes.

A secondary PCR was carried out using the thus-obtained product of the primary PCR. A PCR was carried out using 1 µl of the reaction mixture after the primary PCR as a template as well as a combination of the mixed primer 4 and a primer C2 attached to LA PCR in vitro cloning kit (Takara Shuzo) under the same conditions as those used for the primary PCR. After removing the overlaid mineral oil, 5 µl of the reaction mixture was subjected to electrophoresis on 1.0% agarose gel. An amplification product was confirmed by staining DNA with ethidium bromide. As a result, an amplification product of about 2 kb was observed and the DNA fragment was designated as 4-3N.

This amplified fragment was excised from the agarose gel, extracted and purified according to a conventional method and ligated to a vector pT7Blue. The ligation mixture was used to transform *Escherichia coli* JM109. The nucleotide sequences of the terminal regions of 4-3 were determined according to the dideoxy chain terminator method using the resulting transformants.

Primers were designed based on the determined sequences of the terminal regions of 4-3N. DNA fragments located upstream and downstream from 4-3N were cloned using LA PCR in vitro cloning kit (Takara Shuzo).

Primers 5 and 6 represented by SEQ ID NOS: 8 and 9, respectively, designed based on the sequence of the region around the N-terminus among the terminal regions of 4-3N determined as described above were used for cloning a DNA fragment located upstream from 4-3N. Cloning was carried out as described above for the cloning of 4-3N except that the temperature for annealing of primers was changed to 55° C. As a result, a DNA fragment of about 1.0 kb was obtained and designated as 4-3UN.

Primers 8 and 9 represented by SEQ ID NOS: 10 and 11, respectively, designed based on the sequence of the region around the C-terminus among the terminal regions of 4-3N determined as described above were used for cloning a DNA fragment located downstream from 4-3N. Cloning was carried out as described above for the cloning of 4-3N except that the temperature for annealing of primers was changed to 55° C. As a result, a DNA fragment of about 2.0 kb was obtained and designated as 4-3C.

Each of the thus-obtained fragments 4-3UN and 4-3C was ligated to a vector pT7Blue (Novagen). The nucleotide sequences were determined according to the dideoxy chain terminator method. Analysis and alignment of the nucleotide sequences of the DNA fragments 4-3N, 4-3UN and 4-3C determined as described above revealed an open reading frame (ORF) that encodes a polypeptide consisting of 951 amino acids. The nucleotide sequence of the open reading frame and the amino acid sequence encoded by the nucleotide sequence of the open reading frame are shown in SEQ ID NOS: 13 and 15, respectively. In 4-3UN, a nucleotide sequence for the amino acid sequence P2, an upstream nucleotide sequence encoding 183 amino acids, and a further upstream SD-like sequence were found. The N-terminal amino acid sequence determined for the α-agarase purified from the microorganism TKR4-3, P2, matched with the sequence of the 184th to 203rd amino acids in the amino acid sequence of SEQ ID NO: 15.

The amino acid sequences of Agarase 1-7 and Agarase 4-3 obtained as described above as well as the nucleotide sequences of the genes have no homology with the amino acid sequences of β-agarases, which are known agarose-digesting enzymes that cleave agarose in a different manner from the agarase of the present invention, and the nucleotide sequences of the genes. Thus, these sequences are considered to be absolutely novel.

EXAMPLE 8

Construction of Plasmid for Expressing α-Agarase 1-7

A primer 10 having a sequence of SEQ ID NO: 18 was synthesized. The primer 10 is a primer that has a recognition sequence for a restriction enzyme NdeI at base numbers 8 to 13 and a nucleotide sequence corresponding to an amino acid sequence of amino acid numbers 28 to 31 in the amino acid sequence of α-Agarase 1-7 (SEQ ID NO: 14) at base numbers 14 to 25.

A PCR was carried out using the primer 10 and the primer 2 (SEQ ID NO: 4) which hybridizes to a portion of the vector pUC19 in pAA1 as well as pAA1 as a template.

10 pmol each of the primer 10 and the primer 2, 10 ng of pAA1 obtained in Example 6 as a template, 5 µl of 10×Ex-Taq buffer, 8 µl of a dNTP mixture and 0.5 µl of TaKaRa ExTaq were added to a 0.5-ml tube for PCR. Sterile water was further added thereto to make the total volume to 50 µl. The tube was placed in an automated gene amplification instrument Thermal Cycler (Takara Shuzo). After denaturing at 94° C. for 2 minutes, a PCR of 25 cycles was performed. Each cycle consisted of 94° C. for 1 minute, 55° C. for 2 minutes and 72° C. for 3 minutes. The PCR product was concentrated and desalted by ethanol precipitation, doubly digested with restriction enzymes NdeI (Takara Shuzo) and BamHI (Takara Shuzo), and then subjected to electrophoresis on 1.0% agarose gel. The NdeI-BamHI digest was separated, extracted and purified. The purified product was mixed with and ligated to pKF19k (Takara Shuzo) digested with NdeI and BamHI using a DNA ligation kit (Takara Shuzo). 10 µl of the ligation mixture was used to transform *Escherichia coli* JM109. Transformants were grown on LB medium containing agar at a concentration of 1.5% (w/v) and kanamycin at a concentration of 50 µg/ml. Plasmids were prepared from white colonies, DNA sequencing was carried out, and a plasmid into which the PCR product was properly inserted was selected and designated as pAA201. pAA201 is a plasmid that encodes an amino acid sequence of amino acid numbers 28 to 925 in the amino acid sequence of α-Agarase 1-7 (SEQ ID NO:14).

The transformant having pAA201 being introduced was inoculated into 2.5 ml of LB broth containing 50 μg/ml kanamycin and 10 mM calcium chloride and cultured at 37° C. overnight. A portion of the culture was inoculated into 2.5 ml of the same fresh medium and cultured at 25° C. until it reached exponential growth phase. At that time, IPTG was added thereto at a final concentration of 1.0 mM. The cultivation was continued at 15° C. overnight to induce the expression of the protein of interest. The cells were then collected by centrifugation and resuspended in 150 μl of a cell destruction solution (20 mM tris-hydrochloride (pH 7.0), 10 mM calcium chloride, 10 mM sodium chloride). The cells were destroyed by sonication. An extract as a supernatant and a precipitate were separated each other by centrifugation and used as samples for the measurement of α-agarase activities using agarose as a substrate. Then, an activity was observed for the extract. The activity contained in 100 ml of the culture was about 25-fold higher than that of the wild type strain TKR1-7AGα.

EXAMPLE 9

Expression System for α-Agarase 1-7 Using pT7BlueT Vector

A primer 11 having a sequence of SEQ ID NO: 19 was synthesized. The primer 11 is a primer that has a nucleotide sequence corresponding to an amino acid sequence of amino acid numbers 28 to 33 in the amino acid sequence of α-Agarase 1-7 (SEQ ID NO: 14) at base numbers 13 to 30.

A PCR was carried out using the primer 11 and the primer 2 as well as pAA1 as a template. The PCR product was separated by electrophoresis on 1.0% agarose gel, extracted and purified. The purified PCR product was ligated to pT7BlueT (Takara Shuzo), a vector designed for cloning, to construct an expression vector. The conditions used for the PCR were those as described in Example 8. DNA sequencing was carried out and a plasmid into which the PCR product was properly inserted was selected.

The selected hybrid plasmid was designated as pAA301. pAA301 is a plasmid that encodes an amino acid sequence of amino acid numbers 28 to 925 in the amino acid sequence of α-Agarase 1-7 (SEQ ID NO:14) like pAA201.

pAA301 was used to transform *Escherichia coli* JM109 and the resulting transformant was inoculated into LB medium containing 50 μg/ml ampicillin and 10 mM calcium chloride. The expression of the protein of interest was induced using IPTG, and the α-agarase activity was determined as described above in Example 8. Then, an activity was observed for the extract. The activity contained in 100 ml of the culture was about 100-fold higher than that of TKR1-7AGα.

EXAMPLE 10

Expression System for α-Agarase 1-7 Using pET16b

A primer 12 having a sequence of SEQ ID NO: 20 was synthesized. The primer 12 is a primer that has a nucleotide sequence complementary to a nucleotide sequence corresponding to amino acid numbers 919 to 924 in the amino acid sequence of α-Agarase 1-7 (SEQ ID NO: 14) at base numbers 17 to 34 and a recognition sequence for a restriction enzyme BamHI at base numbers 9 to 14.

A PCR was carried out using the primer 10 (SEQ ID NO: 18) and the primer 12 (SEQ ID NO: 20) as well as pAA1 as a template under conditions as described in Example 8. The amplified fragment was concentrated and desalted by ethanol precipitation, digested with NdeI (Takara Shuzo) and BamHI (Takara Shuzo), separated by agarose gel electrophoresis, extracted and purified. The product was ligated to pET16b (Takara Shuzo) digested with NdeI and BamHI. The resulting hybrid plasmid was designated as pAA401. pAA401 is a plasmid that encodes an amino acid sequence of amino acid numbers 28 to 925 in the amino acid sequence of α-Agarase 1-7 (SEQ ID NO:14) like pAA201 and pAA301.

pAA401 was used to transform *Escherichia coli* BL21 (DE3)pLysS and the resulting transformant was used to determine the α-agarase activity as described above in Example 8 except that ampicillin was used as a drug in place of kanamycin. Then, an activity was observed for the extract. The activity contained in 100 ml of the culture was about 100-fold higher than that of TKR1-7AGα.

EXAMPLE 11

Construction of Plasmid for Expressing α-Agarase 4-3

A primer 13 having a sequence of SEQ ID NO: 21 and a primer 14 having a sequence of SEQ ID NO: 22 were synthesized.

The primer 13 is a primer that has a recognition sequence for a restriction enzyme NdeI at base numbers 12 to 17 and a nucleotide sequence corresponding to an amino acid sequence of amino acid numbers 184 to 187 in the amino acid sequence of α-Agarase 4-3 (SEQ ID NO: 15) at base numbers 18 to 29.

The primer 14 is a primer that has a recognition sequence for a restriction enzyme BamHI at base numbers 8 to 13 and a sequence that hybridizes to a region downstream from the open reading frame of the α-Agarase 4-3 gene obtained by cloning.

A PCR was carried out using the primers 13 and 14 as well as the chromosomal DNA from the wild type strain TKR4-3AGα as a template. A reaction mixture for PCR containing 10 pmol each of the primers 13 and 14, 10 ng of the chromosomal DNA from the wild type strain TKR4-3AGα digested with a restriction enzyme BamHI as a template and ExTaq (Takara Shuzo) was prepared. After denaturing at 94° C. for 2 minutes, a PCR of 25 cycles was performed. Each cycle consisted of 94° C. for 1 minute, 50° C. for 2 minutes and 72° C. for 3 minutes. The resulting PCR product was concentrated by ethanol precipitation and doubly digested with restriction enzymes NdeI (Takara Shuzo) and BamHI (Takara Shuzo). The NdeI-BamHI digest was separated by electrophoresis on 1.0% agarose gel, extracted and purified. A hybrid plasmid with pKF19k was constructed as described in Example 8 and transformation of *Escherichia coli* JM109 was carried out. Plasmids were prepared from the resulting transformants, and a plasmid into which the PCR product was inserted in a proper direction was selected and designated as pAH101. pAH101 is a plasmid that encodes an amino acid sequence of amino acid numbers 184 to 951 in the amino acid sequence of α-Agarase 4-3 (SEQ ID NO:15).

*Escherichia coli* transformed with the plasmid pAH101 is designated and indicated as *Escherichia coli* JM109/pAH101, and deposited under Budapest Treaty on Jan. 27, 2000 at the National Institute of Bioscience and Human-Technology, Agency of Industrial Science and Technology, Ministry of International Trade and Industry, 1-3, Higashi 1-chome, Tsukuba-shi, Ibaraki, Japan under accession number FERM BP-7008.

The α-agarase activity was determined for the transformant harboring pAH101 as described above in Example 8. Then, an activity was observed for the extract. The activity contained in 100 ml of the culture was about 15-fold higher than that of the wild type strain TKR4-3AGα.

EXAMPLE 12

Expression System for α-Agarase 4-3 Using pET16b

A primer 15 having a sequence of SEQ ID NO: 23 was synthesized.

The primer 15 is a primer that has a recognition sequence for a restriction enzyme BamHI at base numbers 10 to 15 and a nucleotide sequence complementary to a nucleotide sequence corresponding to an amino acid sequence of amino acid numbers 945 to 950 in the amino acid sequence of α-Agarase 4-3 (SEQ ID NO: 15) at base numbers 18 to 35.

A PCR was carried out using the primers 13 and 15 as well as the chromosomal DNA from the wild type strain TKR4-3AGα described in Example 11 as a template under conditions as described in Example 8. The amplified fragment was concentrated by ethanol precipitation, digested with NdeI and BamHI, separated by agarose gel electrophoresis, extracted and purified. The product was ligated to pET16b (Takara Shuzo) digested with NdeI and BamHI. The resulting hybrid plasmid was designated as pAH201. pAH201 is a plasmid that encodes an amino acid sequence of amino acid numbers 184 to 950 in the amino acid sequence of α-Agarase 4-3 (SEQ ID NO:15).

pAH201 was used to transform *Escherichia coli* BL21 (DE3)pLysS and the resulting transformant was used to determine the α-agarase activity described above in Example 8 except that ampicillin was used as a drug in place of kanamycin. Then, an activity was observed for the extract. The activity contained in 100 ml of the culture was about 75-fold higher than that of TKR4-3AGα.

EXAMPLE 13

Activity of Modified Protein

A modified protein was prepared by means of genetic engineering as described below. The α-agarase activity of the modified protein was determined.

A primer 16 having a sequence of SEQ ID NO: 24 was synthesized.

The primer 16 is a primer that has a nucleotide sequence corresponding to an amino acid sequence of amino acid numbers 172 to 174 in the amino acid sequence of α-Agarase 1-7 (SEQ ID NO: 14) at base numbers 3 to 11, a nucleotide sequence corresponding to an amino acid sequence of amino acid numbers 177 to 181 in the amino acid sequence of α-Agarase 1-7 (SEQ ID NO: 14) at base numbers 18 to 32 and a recognition sequence for a restriction enzyme NdeI at base numbers 12 to 17.

A PCR was carried out using the primer 16 and the primer 2 (SEQ ID NO: 4) as well as pAA1 as a template. The product was ligated to pKF19k, and transformation of *Escherichia coli* JM109 was carried out as described in Example 8. Plasmids were prepared from the resulting transformants. A hybrid plasmid obtained by confirming the DNA sequence at the connection site was designated as pAA501. pAA501 is a plasmid that encodes a polypeptide in which a portion up to amino acid number 176 in α-Agarase 1-7 is deleted, i.e., an amino acid sequence of amino acid numbers 177 to 925 in SEQ ID NO:14.

*Escherichia coli* JM109 transformed with pAA501 was cultured as described in Example 8 and the expression of the protein encoded by pAA501 was induced using IPTG, and the activity was determined. Then, an α-agarase activity was observed for the extract.

EXAMPLE 14

Southern Hybridization

Southern hybridization was carried out against the chromosomal DNA from the wild type strain TKR1-7AGα using the fragment inserted in an α-Agarase 4-3 clone pAH101 as a probe. The following procedure was carried out according to the protocol for DIG DNA labeling/detection kit (Roche). In this case, pAH101 was digested with restriction enzymes NdeI and BamHI. The resulting DNA fragment of about 2.4 kb was separated by agarose gel electrophoresis, extracted and purified. About 1.0 µg of the purified fragment was labeled according to the protocol for the above-mentioned kit and used as a probe.

About 2.0 µg of the chromosomal DNA from TKR1-7AGα was digested with BamHI and electrophoresed on 1.0% agarose gel. The DNA fragments were transferred onto a nitrocellulose membrane (Amersham) using 0.4N sodium hydroxide according to the conventional method. Prehybridization was then carried out at 68° C. for 1 hour. The labeled probe was heat-denatured and added thereto. Hybridization was carried out at 68° C. overnight in a solution containing 6×SSC, 0.5% SDS, 5× Denhardt's and 100 mg/ml herring sperm DNA. The membrane was washed twice in 2×SSC, 0.1% (w/v) SDS for 5 minutes at room temperature followed by twice in 0.1×SSC, 0.1% (w/v) SDS for 15 minutes at 68° C. to eliminate excess probe. A detection reaction was then carried out according to the protocol. As a result, a band was observed at a position corresponding to about 7.2 kb. As described above, a gene encoding an active α-agarase, the α-agarase gene from the wild type strain TKR1-7AGα, could be detected by conducting hybridization using the α-Agarase 4-3 gene as a probe under stringent conditions. Comparison of the entire sequences of the open reading frames for Agarase 1-7 and Agarase 4-3 revealed that they share homologies in the amino acid sequence and the nucleotide sequence of the gene of 51% and 61%, respectively.

EXAMPLE 15

Preparation of Deleted Forms of α-Agarase

Proteins each having deletion at N-terminus as described below were made by means of genetic engineering, and the α-agarase activities for the respective proteins were determined.

(1) α-Agarase Activities of Deleted Forms of α-Agarase 1-7

A primer 17 (SEQ ID NO:25) has nucleotide sequences corresponding to amino acid sequences of amino acid numbers 197 to 200 and 201 to 206 in the amino acid sequence of α-Agarase 1-7 (SEQ ID NO: 14) at base numbers 1 to 12 and 19 to 36 and a recognition sequence for a restriction enzyme NdeI at base numbers 13 to 18. A PCR was carried out using this primer and the primer 2 (SEQ ID NO: 4) as well as the plasmid pAA1 as a template as follows. 10 pmol each of the primer 17 and the primer 2, 10 ng of pAA1 as a template, 5 µl of 10×ExTaq buffer, 8 µl of a dNTP mixture and 0.5 µl of TaKaRa ExTaq were added to a 0.5-ml tube for PCR. Sterile water was further added thereto to make the total volume to 50 µl. The tube was placed in an automated gene amplification instrument Thermal Cycler (Takara Shuzo). After denaturing at 94° C. for 2 minutes, a PCR of 25 cycles was performed. Each cycle consisted of 94° C. for 1 minute, 55° C. for 2 minutes and 72° C. for 3 minutes. The PCR product was concentrated and desalted by ethanol precipitation, and doubly digested with restriction enzymes NdeI (Takara Shuzo) and BamHI (Takara Shuzo). The digest was subjected to electrophoresis on 1.0% agarose gel. The PCR product digested with NdeI and BamHI was extracted and purified. The purified PCR product was mixed with and ligated to pKF19k (Takara Shuzo) digested with NdeI and BamHI using a DNA ligation kit (Takara Shuzo). 10 μl of the ligation mixture was used to transform Escherichia coli JM109. Transformants were grown on LB medium containing agar at a concentration of 1.5% (w/v) and kanamycin at a concentration of 50 μg/ml. Plasmids were prepared from white colonies, nucleotide sequences of the fragments inserted into the plasmids were determined, and a plasmid into which the PCR product was inserted was selected and designated as pAA-deN1. The protein expressed from this plasmid is one in which a portion up to amino acid number 200 is deleted in α-Agarase 1-7.

A transformant obtained by introducing pAA-deN1 into Escherichia coli was inoculated into 2.5 ml of LB broth containing 50 μg/ml kanamycin and 10 mM calcium chloride and cultured at 37° C. overnight. A portion of the culture was inoculated into 2.5 ml of the same fresh medium and cultured at 25° C. until it reached exponential growth phase. At that time, IPTG was added thereto at a final concentration of 1.0 mM. The cultivation was continued at a lower cultivation temperature, 15° C., overnight to induce the expression of the protein of interest. The cells were then collected by centrifugation and suspended in 150 μl of a cell destruction solution (20 mM tris-hydrochloride (pH 7.0), 10 mM calcium chloride, 10 mM sodium chloride). The cells were destroyed by sonication. A cell-free extract as a supernatant and a precipitate were separated each other by centrifugation and used as samples for the measurement of α-agarase activities using agarose as a substrate according to the method as described above. Then, an activity was observed for the cell-free extract.

Deleted forms were made in a similar manner and their α-agarase activities were determined.

A primer 18 (SEQ ID NO:26) has nucleotide sequences corresponding to amino acid sequences of amino acid numbers 332 to 334 and 335 to 340 in the amino acid sequence of α-Agarase 1-7 (SEQ ID NO: 14) at base numbers 3 to 11 and 18 to 35 and a recognition sequence for a restriction enzyme NdeI at base numbers 12 to 17. A hybrid plasmid constructed by using this primer in place of the primer 17 was designated as pAA-deN2. The protein expressed from this plasmid is one in which a portion up to amino acid number 334 is deleted in α-Agarase 1-7.

A primer 19 (SEQ ID NO:27) has nucleotide sequences corresponding to amino acid sequences of amino acid numbers 376 to 378 and 379 to 385 in the amino acid sequence of α-Agarase 1-7 (SEQ ID NO: 14) at base numbers 2 to 10 and 18 to 38 and a recognition sequence for a restriction enzyme NdeI at base numbers 11 to 16. A hybrid plasmid constructed by using this primer in place of the primer 17 was designated as pAA-deN3. The protein expressed from this plasmid is one in which a portion up to amino acid number 378 is deleted in α-Agarase 1-7. The results for the α-agarase activities expressed by transformants having these plasmids being introduced are summarized in Table 2.

(2) α-Agarase Activities of Deleted Forms of α-Agarase 4-3

Deleted forms of Agarase 4-3 were made as described above for Agarase 1-7.

A primer 20 (SEQ ID NO:28) has nucleotide sequences corresponding to amino acid sequences of amino acid numbers 247 to 250 and 251 to 255 in the amino acid sequence of α-Agarase 4-3 (SEQ ID NO: 15) at base numbers 1 to 12 and 19 to 33 and a recognition sequence for a restriction enzyme NdeI at base numbers 13 to 18. A PCR was carried out using this primer and the primer 2 (SEQ ID NO: 4) as well as the plasmid pAH101 described in Example 11 as a template. The procedure as described in Example 15 (1) was then carried out to construct a hybrid plasmid with pKF19k, which was designated as pAH-deN1. A protein in which a polypeptide up to amino acid number 250 is deleted in the amino acid sequence of α-Agarase 4-3 (SEQ ID NO:15) is expressed from Escherichia coli JM109 having this hybrid plasmid being introduced. The activity was determined for the transformant as described in Example 15 (1). Then, an α-agarase activity was observed for the cell-free extract.

A primer 21 (SEQ ID NO:29) has nucleotide sequences corresponding to amino acid sequences of amino acid numbers 361 to 364 and 365 to 370 in the amino acid sequence of α-Agarase 4-3 (SEQ ID NO: 15) at base numbers 3 to 14 and 21 to 38 and a recognition sequence for a restriction enzyme NdeI at base numbers 15 to 20. A plasmid constructed by using this primer in place of the primer 20 was designated as pAH-deN2. A protein in which a polypeptide up to amino acid number 364 is deleted in the amino acid sequence of α-Agarase 4-3 (SEQ ID NO:15) is expressed from Escherichia coli JM109 having this plasmid being introduced.

A primer 22 (SEQ ID NO:30) has nucleotide sequences corresponding to amino acid sequences of amino acid numbers 406 to 408 and 409 to 413 in the amino acid sequence of α-Agarase 4-3 (SEQ ID NO: 15) at base numbers 3 to 11 and 18 to 32 and a recognition sequence for a restriction enzyme NdeI at base numbers 12 to 17. A plasmid constructed by using this primer in place of the primer 20 was designated as pAH-deN3. A protein in which a polypeptide up to amino acid number 408 is deleted in the amino acid sequence of α-Agarase 4-3 (SEQ ID NO:15) is expressed from this plasmid being introduced. The results for the α-agarase activities expressed by transformants having these plasmids being introduced are summarized in Table 2.

TABLE 2

| | α-Agarase activity |
|---|---|
| pAA-deN1 | + |
| pAA-deN2 | + |
| pAA-deN3 | − |
| pAH-deN1 | + |
| pAH-deN2 | + |
| pAH-deN3 | − |

The present invention provides a novel α-agarase. It is possible to produce agarooligosaccharides with low degrees of polymerization having 3,6-anhydro-L-galactose at their reducing ends (e.g., agarobiose and agarotetraose) directly from agarose by using said enzyme. The agarooligosaccharides produced using the α-agarase of the present invention have physiological activities such as an apoptosis-inducing activity, a carcinostatic activity, various antioxidant activities, an immunoregulatory activity and an antiallergic activity. Thus, they are useful in the fields of pharmaceutical compositions, foods and drinks.

The present invention discloses an amino acid sequence and a nucleotide sequence for an α-agarase for the first time. Thus, it is possible to provide a gene encoding a polypeptide having an α-agarase activity. The present invention also provides an industrially advantageous method for producing a polypeptide having an α-agarase activity by genetic engineering using said gene.

Furthermore, addition of agarose to a medium for inducing the production of the α-agarase is not required in the production method by genetic engineering using said gene. Thus, it is considered that labor can be saved upon cultivation and the enzyme is readily purified.

In addition, based on the fact that the present invention provides an α-agarase gene for the first time, the present invention provides, based on the information on said gene, a recombinant polypeptide encoded by the gene, an antibody that specifically binds to the polypeptide or a fragment thereof, as well as a probe or a primer that specifically hybridize to α-agarase.

Sequence Listing Free Text

SEQ ID NO:1: N-terminal amino acid sequence of agarase 1-7.
SEQ ID NO:2: N-terminal amino acid sequence of agarase 4-3.
SEQ ID NO:3: Designed oligonucleotide primer for PCR using pAA1 as template.
SEQ ID NO:4: Designed oligonucleotide primer for PCR using pAA1 as template.
SEQ ID NO:5: Designed oligonucleotide primer for DNA sequencing of pAA1.
SEQ ID NO:6: Designed oligonucleotide primer for amplifying DNA fragment 4-3N.
SEQ ID NO:7: Designed oligonucleotide primer for amplifying DNA fragment 4-3N.
SEQ ID NO:8: Designed oligonucleotide primer for cloning DNA fragment 4-3UN.
SEQ ID NO:9: Designed oligonucleotide primer for cloning DNA fragment 4-3UN.
SEQ ID NO:10: Designed oligonucleotide primer for cloning DNA fragment 4-3C.
SEQ ID NO:11: Designed oligonucleotide primer for cloning DNA fragment 4-3C.
SEQ ID NO:12: Nucleotide sequence of ORF in agarase 1-7 gene.
SEQ ID NO:13: Nucleotide sequence of ORF in agarase 4-3 gene.
SEQ ID NO:14: Amino acid sequence of agarase 1-7.
SEQ ID NO:15: Amino acid sequence of agarase 4-3.
SEQ ID NO:16: Designed oligonucleotide primer for amplifying DNA fragment from 16S ribosomal.
SEQ ID NO:17: Designed oligonucleotide primer for amplifying DNA fragment from 16S ribosomal.
SEQ ID NO:18: Designed oligonucleotide for constructing plasmid for expressing agarase 1-7.
SEQ ID NO:19: Designed oligonucleotide for constructing plasmid for expressing agarase 1-7.
SEQ ID NO:20: Designed oligonucleotide for constructing plasmid for expressing agarase 1-7.
SEQ ID NO:21: Designed oligonucleotide for constructing plasmid for expressing agarase 4-3.
SEQ ID NO:22: Designed oligonucleotide for constructing plasmid for expressing agarase 4-3.
SEQ ID NO:23: Designed oligonucleotide for constructing plasmid for expressing agarase 4-3.
SEQ ID NO:24: Designed oligonucleotide for constructing plasmid for expressing agarase 1-7.
SEQ ID NO:25: Designed oligonucleotide for constructing plasmid for expressing agarase 1-7.
SEQ ID NO:26: Designed oligonucleotide for constructing plasmid for expressing agarase 1-7.
SEQ ID NO:27: Designed oligonucleotide for constructing plasmid for expressing agarase 1-7.
SEQ ID NO:28: Designed oligonucleotide for constructing plasmid for expressing agarase 4-3.
SEQ ID NO:29: Designed oligonucleotide for constructing plasmid for expressing agarase 4-3.
SEQ ID NO:30: Designed oligonucleotide for constructing plasmid for expressing agarase 4-3.

What is claimed is:

1. An isolated polypeptide having an α-agarase activity, selected from the group consisting of:
   (a) a polypeptide comprising the amino acid sequence consisting of 767 residues from amino acid number 184 to amino acid number 950 in the amino acid sequence of SEQ ID NO:15; and
   (b) a polypeptide containing the amino acid sequence consisting of 586 residues from amino acid number 365 to amino acid number 950 in the amino acid sequence of SEQ ID NO:15.

2. A method for producing an agarooligosaccharide, comprising digesting agarose using the α-agarase of claim 1 and collecting an agarooligosaccharide from the resulting digest.

* * * * *